(12) United States Patent
Noll

(10) Patent No.: US 8,728,802 B2
(45) Date of Patent: May 20, 2014

(54) ANGLED REACTION VESSEL

(75) Inventor: Anthony P. Noll, Augusta, KY (US)

(73) Assignee: Biomass Worldwide Group Limited, Cheadle and Gatley (GB)

( * ) Notice: Subject to any disclaimer, the term of this patent is extended or adjusted under 35 U.S.C. 154(b) by 632 days.

(21) Appl. No.: 12/826,347

(22) Filed: Jun. 29, 2010

(65) Prior Publication Data

US 2010/0261895 A1    Oct. 14, 2010

Related U.S. Application Data

(63) Continuation-in-part of application No. 11/355,632, filed on Feb. 15, 2006, now Pat. No. 7,745,208.

(51) Int. Cl.
 C12M 3/00    (2006.01)
 C12M 1/00    (2006.01)
 C12M 3/04    (2006.01)
 C12M 1/12    (2006.01)
 C12M 1/107   (2006.01)

(52) U.S. Cl.
 CPC ............ *C12M 27/10* (2013.01); *C12M 21/00* (2013.01); *C12M 23/06* (2013.01); *C12M 21/04* (2013.01)
 USPC ............. 435/290.3; 435/289.1; 435/298.1; 435/298.2; 435/290.1

(58) Field of Classification Search
 CPC ...... C12M 27/10; C12M 21/00; C12M 23/06; C12M 21/04; C12M 17/02; C12M 3/28
 USPC ........... 435/290.3, 289.1, 298.1, 298.2, 290.1
 See application file for complete search history.

(56) References Cited

U.S. PATENT DOCUMENTS

| | | | |
|---|---|---|---|
| 742,226 A | 10/1903 | Peck et al. | |
| 1,938,647 A | 12/1933 | Earp-Thomas | |
| 2,317,992 A | 5/1943 | Grether | |
| 2,823,106 A | 2/1958 | Pierson | |
| 2,969,277 A | 1/1961 | Carlsson et al. | |

(Continued)

FOREIGN PATENT DOCUMENTS

| | | |
|---|---|---|
| EP | 0277507 A2 | 1/1993 |
| EP | 0549356 A1 | 6/1993 |

(Continued)

OTHER PUBLICATIONS

International Bureau, Notification Concerning Transmittal of International Preliminary Report on Patentability, Written Opinion of the International Searching Authority, International Preliminary Report, International Application No. PCT/US2007/061827, Aug. 28, 2008 date of mailing, 6 pages.

(Continued)

*Primary Examiner* — Nathan Bowers
(74) *Attorney, Agent, or Firm* — Wood Herron & Evans, LLP

(57) ABSTRACT

An improved apparatus and process for treating biomass bearing material including municipal solid waste (MSW). The apparatus includes a reaction vessel configured for rotation and steam injection, with helically arranged auger vanes attached to the internal walls of the vessel, a self aligning door. Embodiments includes various of a heated jacket, modified raised projections on the top edge of the auger vanes, a modified door, modified door sealing assembly, and a process of quick charging the interior of the vessel with steam.

15 Claims, 14 Drawing Sheets

(56) References Cited

U.S. PATENT DOCUMENTS

| | | | |
|---|---|---|---|
| 3,055,744 A | 9/1962 | Peterson | |
| 3,057,769 A | 10/1962 | Sandberg | |
| 3,070,156 A | 12/1962 | Starrett | |
| 3,235,369 A | 2/1966 | Eweson | |
| 3,236,604 A | 2/1966 | Pierson | |
| 3,524,594 A | 8/1970 | Anderson et al. | |
| 3,549,010 A | 12/1970 | Marsh et al. | |
| 3,549,092 A | 12/1970 | Baxter, Jr. | |
| 3,587,851 A | 6/1971 | Anderson | |
| 3,595,488 A | 7/1971 | Blakely et al. | |
| 3,597,308 A | 8/1971 | Brooks | |
| 3,643,797 A | 2/1972 | Berkowitz et al. | |
| 3,668,286 A | 6/1972 | Brooks et al. | |
| 3,714,038 A | 1/1973 | Marsh | |
| 3,725,538 A | 4/1973 | Brewer | |
| 3,736,223 A | 5/1973 | Marsh | |
| 3,741,863 A | 6/1973 | Brooks | |
| 3,833,117 A | 9/1974 | Mackenzie et al. | |
| 3,849,246 A | 11/1974 | Raymond et al. | |
| 3,932,166 A | 1/1976 | Vignovich et al. | |
| 3,939,286 A | 2/1976 | Jelks | |
| 3,961,913 A | 6/1976 | Brenneman et al. | |
| 3,993,577 A | 11/1976 | Black et al. | |
| RE29,156 E | 3/1977 | Marsh | |
| 4,010,098 A | 3/1977 | Fassell | |
| 4,033,907 A | 7/1977 | Wolf | |
| 4,044,695 A | 8/1977 | Mackenzie et al. | |
| 4,056,380 A | 11/1977 | Thiac | |
| 4,079,837 A | 3/1978 | Grube et al. | |
| 4,106,627 A | 8/1978 | Watanabe et al. | |
| 4,111,800 A | 9/1978 | Harendza-Harinxma | |
| 4,121,383 A * | 10/1978 | Holmes et al. | 49/395 |
| 4,152,119 A | 5/1979 | Schulz | |
| 4,157,961 A | 6/1979 | Borst | |
| 4,185,680 A | 1/1980 | Lawson | |
| 4,203,755 A * | 5/1980 | Ruckstuhl | 71/9 |
| 4,212,950 A * | 7/1980 | Adams | 435/289.1 |
| 4,225,457 A | 9/1980 | Schulz | |
| 4,235,707 A | 11/1980 | Burke, Jr. | |
| 4,264,352 A | 4/1981 | Houser | |
| 4,297,322 A | 10/1981 | Liu | |
| 4,312,701 A | 1/1982 | Campbell | |
| 4,321,150 A | 3/1982 | McMullen | |
| 4,342,830 A | 8/1982 | Holloway | |
| 4,368,079 A | 1/1983 | Rugg et al. | |
| 4,440,635 A | 4/1984 | Reiniger | |
| 4,461,648 A | 7/1984 | Foody | |
| 4,465,591 A | 8/1984 | Holz et al. | |
| 4,468,256 A | 8/1984 | Hinger | |
| 4,478,644 A | 10/1984 | Berger et al. | |
| 4,483,704 A | 11/1984 | Easter, II | |
| 4,540,467 A | 9/1985 | Grube et al. | |
| 4,540,495 A | 9/1985 | Holloway | |
| 4,566,942 A | 1/1986 | Holz | |
| 4,570,861 A | 2/1986 | Zentgraf et al. | |
| 4,607,797 A | 8/1986 | Enikolopow et al. | |
| 4,632,729 A | 12/1986 | Laakso | |
| 4,637,835 A | 1/1987 | Nagle | |
| 4,650,125 A | 3/1987 | Pellhammer | |
| 4,699,632 A | 10/1987 | Babu et al. | |
| 4,750,437 A | 6/1988 | Rouse | |
| 4,816,117 A | 3/1989 | Pfalzer et al. | |
| 4,836,918 A | 6/1989 | Szikriszt | |
| 4,842,877 A | 6/1989 | Tyson | |
| 4,844,351 A | 7/1989 | Holloway | |
| 4,925,571 A | 5/1990 | Jacob et al. | |
| 4,949,653 A | 8/1990 | Rast | |
| 4,974,781 A | 12/1990 | Placzek | |
| 4,977,943 A | 12/1990 | Miyabe | |
| 5,003,143 A | 3/1991 | Marks et al. | |
| 5,009,370 A | 4/1991 | Mackenzie | |
| 5,013,458 A | 5/1991 | Christy, Sr. et al. | |
| 5,023,097 A | 6/1991 | Tyson | |
| 5,050,375 A | 9/1991 | Dickinson | |
| 5,104,419 A | 4/1992 | Funk | |
| 5,114,488 A | 5/1992 | Huber et al. | |
| 5,116,363 A | 5/1992 | Romweber et al. | |
| 5,119,994 A | 6/1992 | Placzek | |
| 5,122,228 A | 6/1992 | Bouchette et al. | |
| 5,143,481 A | 9/1992 | Schumacher et al. | |
| 5,148,999 A | 9/1992 | Curfman et al. | |
| 5,190,226 A | 3/1993 | Holloway | |
| 5,196,069 A | 3/1993 | Cullingford et al. | |
| 5,196,620 A | 3/1993 | Gustin et al. | |
| 5,217,688 A | 6/1993 | Lersner | |
| 5,253,764 A | 10/1993 | Gement | |
| 5,258,293 A | 11/1993 | Lynd et al. | |
| 5,280,757 A | 1/1994 | Carter et al. | |
| 5,300,438 A | 4/1994 | Auspurger et al. | |
| 5,361,994 A | 11/1994 | Holloway | |
| 5,412,881 A | 5/1995 | Romweber et al. | |
| 5,427,650 A | 6/1995 | Holloway | |
| 5,427,738 A | 6/1995 | Galloway | |
| 5,429,645 A | 7/1995 | Benson et al. | |
| 5,439,823 A * | 8/1995 | Sayama | 435/286.1 |
| 5,445,329 A | 8/1995 | Anderson | |
| 5,456,553 A | 10/1995 | Li et al. | |
| 5,459,071 A | 10/1995 | Finn | |
| 5,480,610 A | 1/1996 | Birkholz et al. | |
| 5,492,407 A | 2/1996 | Gement | |
| 5,501,719 A | 3/1996 | Shida et al. | |
| 5,504,259 A | 4/1996 | Diebold et al. | |
| 5,534,437 A | 7/1996 | Arrau | |
| 5,540,391 A | 7/1996 | Anderson | |
| 5,556,445 A | 9/1996 | Quinn et al. | |
| 5,587,157 A | 12/1996 | Cox et al. | |
| 5,589,164 A | 12/1996 | Cox et al. | |
| 5,589,391 A | 12/1996 | Fink | |
| 5,602,297 A | 2/1997 | Wang | |
| 5,613,306 A | 3/1997 | Romweber et al. | |
| 5,615,626 A | 4/1997 | Floyd et al. | |
| 5,658,097 A | 8/1997 | Komori et al. | |
| 5,705,216 A | 1/1998 | Tyson | |
| 5,711,817 A | 1/1998 | Titmas | |
| 5,732,892 A | 3/1998 | Neier | |
| 5,772,847 A | 6/1998 | Simpson et al. | |
| 5,795,479 A | 8/1998 | Vogt et al. | |
| 5,822,881 A | 10/1998 | Romweber et al. | |
| 5,844,008 A | 12/1998 | McMillan | |
| 5,879,637 A | 3/1999 | Titmas | |
| 6,123,747 A | 9/2000 | Kim et al. | |
| 6,197,081 B1 | 3/2001 | Schmidt | |
| 6,207,015 B1 | 3/2001 | Templer et al. | |
| 6,238,516 B1 | 5/2001 | Watson et al. | |
| 6,245,195 B1 | 6/2001 | Marwah | |
| 6,267,309 B1 | 7/2001 | Chieffalo et al. | |
| 6,306,248 B1 | 10/2001 | Elay | |
| 6,328,234 B1 | 12/2001 | Saucier et al. | |
| 6,379,527 B1 | 4/2002 | Vogt et al. | |
| 6,397,492 B1 | 6/2002 | Malley | |
| 6,409,841 B1 | 6/2002 | Lombard | |
| 6,458,240 B1 | 10/2002 | Bouchette et al. | |
| 6,730,223 B1 | 5/2004 | Anderson et al. | |
| 7,371,566 B1 | 5/2008 | Craven, Jr. | |
| 7,745,208 B2 | 6/2010 | Noll | |
| 7,967,877 B2 | 6/2011 | Noll et al. | |
| 2005/0166812 A1 | 8/2005 | Noll et al. | |
| 2006/0112616 A1 | 6/2006 | Noll et al. | |
| 2006/0112749 A1 | 6/2006 | Noll et al. | |
| 2007/0190643 A1 | 8/2007 | Noll et al. | |

FOREIGN PATENT DOCUMENTS

| | | |
|---|---|---|
| EP | 1118706 A2 | 7/2001 |
| EP | 1700610 A2 | 9/2006 |
| FR | 2522013 A1 | 8/1983 |
| GB | 809329 | 2/1959 |
| WO | 9212738 A1 | 8/1992 |
| WO | 9323167 A1 | 11/1993 |
| WO | 9426320 A1 | 11/1994 |
| WO | 9732077 A1 | 9/1997 |
| WO | 9947282 A1 | 9/1999 |
| WO | 0072987 A1 | 12/2000 |
| WO | 0224354 A1 | 3/2002 |

(56) References Cited

FOREIGN PATENT DOCUMENTS

| WO | 03025101 | A2 | 3/2003 |
|---|---|---|---|
| WO | 03035970 | A1 | 5/2003 |
| WO | 2006015423 | A1 | 2/2006 |

OTHER PUBLICATIONS

United States Patent and Trademark Office, Official Action directed to U.S. Appl. No. 11/296,585, mailed Jul. 22, 2008, 19 pages.
United States Patent and Trademark Office, Official Action directed to U.S. Appl. No. 11/296,586, mailed Sep. 4, 2008, 16 pages.
United States Patent and Trademark Office, Official Action directed to U.S. Appl. No. 10/713,557, mailed Nov. 13, 2003, 9 pages.
United States Patent and Trademark Office, Official Action directed to U.S. Appl. No. 11/296,586, mailed Apr. 16, 2009, 11 pages.
United States Patent and Trademark Office, Official Action directed to U.S. Appl. No. 11/355,632 mailed Feb. 19, 2009, 15 pages.
United States Patent and Trademark Office, Official Action directed to U.S. Appl. No. 11/296,585, mailed Jan. 21, 2009, 12 pages.
United States Patent and Trademark Office, Official Action directed to U.S. Appl. No. 11/296,585, mailed Jan. 25, 2010, 14 pages.
United States Patent and Trademark Office, Official Action directed to U.S. Appl. No. 11/296,585, mailed Jun. 24, 2009, 31 pages.
United States Patent and Trademark Office, Official Action directed to U.S. Appl. No. 11/355,632, mailed Sep. 2, 2009, 26 pages.
United States Patent and Trademark Office, Advisory Action directed to U.S. Appl. No. 11/355,632 mailed Sep. 17, 2009, 3 pages.
United States Patent and Trademark Office, Advisory Action directed to U.S. Appl. No. 11/355,632 mailed Dec. 30, 2009, 3 pages.
United States Patent and Trademark Office, Notice of Allowance and Fees Due directed to U.S. Appl. No. 11/355,632 mailed Feb. 17, 2010, 6 pages.
International Bureau, Notification Concerning Transmittal of International Preliminary Report on Patentability, Written Opinion of the International Searching Authority, International Preliminary Report, International Application No. PCT/US2011/042184, Oct. 27, 2011 date of mailing, 8 pages.

* cited by examiner

ANGLED REACTION VESSEL

RELATED APPLICATION

This application claims the benefit of U.S. application Ser. No. 11/355,632 filed on Feb. 16, 2006 (and having Publication No. 2007/01990643), the disclosure of which is expressly incorporated by reference herein in its entirety. Said application will issue as U.S. Pat. No. 7,745,208 on Jun. 29, 2010.

FIELD OF THE INVENTION

The present invention generally relates to processing biomass bearing material including municipal solid waste (MSW), and more particularly relates to reaction vessels for treating biomass bearing material and other material containing cellulose or biomass in a heated and pressurized process.

BACKGROUND OF THE INVENTION

Handling solid waste is an increasingly difficult problem. A majority of the United States' solid waste is disposed of in landfills. However, nationwide the availability of solid waste landfills is decreasing as landfills reach capacity and close, while opening new landfills is difficult due to regulations. The national average for solid waste disposal fees has increased several times since 1985. Such fees, called tipping fees, are expected to rise even further with increased demand for land fill space.

These and other issues pertaining to the environmental impact of landfills have prompted solid waste managers to seek methods to reduce volumes and disposal costs of municipal solid waste (MSW). Some experts contend that there is no waste volume problem, but there exists a sorting and recycling problem.

There have been a number of suggestions, some patented, for treating and/or reprocessing MSW. These often involve some form of heat and pressure, and often a reaction vessel that may rotate. Although MSW varies in composition, there is a certain norm to its content. The cellulosic fraction represents approximately seventy percent of the bulk of typical MSW. Other forms of waste have a cellulosic fraction and can be processed in the same process that works for MSW or other biomass bearing material. These include sewer sludge, industrial waste streams, industrial byproducts, agricultural waste and byproducts, food processing waste and byproducts, and other sources. The cellulosic fraction of the biomass bearing material includes all portions that are organic, putrescible, or of biological origin which could eventually decay in a landfill and the decay could eventually lead to the production of methane gas and leachate. It is to be understood that the use of the term "biomass bearing material" in this application encompasses MSW as well as other forms of waste having a cellulosic fraction.

Separating this cellulosic fraction into reusable products can alleviate much of the pollution resulting from the disposal of organic bearing waste. The quality of the cellulosic fraction that is separated from the biomass bearing material determines how it may be used. Higher quality cellulosic fractions bearing less contamination from plastic and other materials will have more uses and be less regulated than lower quality fractions. For example, in the energy industry, solid waste may be mass burned as a fuel source in specially built incinerators. The energy industry may also utilize refuse derived fuels which have had some separation of metal and glass materials before burning. Due to the remaining plastic contaminants in solid waste and refuse derived fuels, these incinerators are also highly regulated and expensive to maintain. However, high quality cellulosic material that has very low contamination from plastic materials may be certified as a renewable organic based fuel that is not as highly regulated. The high quality cellulosic fraction of biomass bearing material may be used as loose or pelletized fuel or feedstock for gasification, bio refineries and conversion into ethanol and other chemicals and fuels. The high quality biomass bearing fraction of MSW could also serve as a source of hydrogen and other liquid, elemental or gaseous products achieved through gasification or other thermal processes, including hydrolysis. In summary, the more effectively that the cellulosic fraction can be removed from the biomass bearing material, the less the waste is likely to contaminate the environment and the more likely the removed fraction can be better utilized on other processes.

Once the cellulosic fraction is removed, the remaining waste material, which includes ferrous and non-ferrous metals, plastics, and textiles, is much reduced in volume and other recoverable fractions of the waste stream can be recovered. Processes are available to recover each of these materials and send them to their respective market. If the cellulosic and recoverable waste streams are removed from biomass bearing material, the volume of such waste streams going to landfills is typically less than fifteen percent of the original amount. This reduction in volume reduces hauling costs and landfill space requirements. Removal of the cellulosic fraction of the biomass bearing material also accomplishes this reduction while reducing polluting effluents, including methane and leachate. Further, if the cellulosic portion is removed from the biomass bearing material, the remaining fraction of inorganic waste could be disposed of in waste sites reserved for construction or other inorganic waste, which is space that is often less regulated and therefore less expensive.

Rotating reaction vessels for older forms of solid waste processing techniques are generally very large steel structures that rotate along their longitudinal access. These reaction vessels have eccentricities in the axis of rotation that are introduced during the manufacture and installation of the vessel or are caused by eccentric or other expansion of the metal vessel during operation. The eccentricities can result in the centerline of the vessel moving a significant distance during rotation of the vessel. These eccentricities can be manifest as asymmetric changes in the vessel body relative to the door opening. These asymmetric changes can decrease the operating efficiency of the vessel by increasing the difficulty of forming an effective seal between the vessel and the door. Moreover, the eccentric movement of the vessel can increase operating costs of the vessel due to stresses that can be transferred to door supporting structures during operation. Thus, a reaction vessel is needed that has decreased eccentricities and/or includes structures that accommodate the eccentricities so as to assist in forming the seal between the door and the vessel and to decrease the stresses transferred to the door supporting structures during operation.

Many prior reaction vessels for treating biomass bearing material utilize inefficient high-pressure steam systems to cook and soften the cellulosic fibers of the biomass bearing material. High-pressure steam vessels are undesirable because 1) they require significant licensing and inspection regimes; 2) they must be built to withstand higher pressure which greatly increases their cost; 3) they require a great amount of energy to generate and maintain the high operating pressures, which results in high operating costs; 4) cycling between the high operating pressures and the emptying pressure results in the inefficient loss of a large amount of energy;

5) high operating pressures present significant safety concerns; and 6) high pressure, high pressure steam results in contamination of the cellulosic fraction such as by melted plastic materials that decreases the quality of the fraction and limits its use as a feedstock for various processes. For example, a cellulosic fraction contaminated with plastic material (or chemicals that are leached from plastic materials when exposed to high pressure and high temperature steam) decrease the likelihood that the fraction can certified as a renewable source of energy under various regulatory guidelines as described above or that it could be used as a feedstock in the chemical or paper reprocessing industries.

In today's industrial world, time, energy, and safety are vital factors when choosing to employ a new industrial system. New industrial systems must operate efficiently and safely and also minimize interaction with their operators so that it can function on a day to day basis in the real world. A reaction vessel that achieves adequate softening, pulverization, and separation of cellulosic fibers while utilizing low pressure steam meet these objectives because the vessel could be lighter, less expensive to construct and operate, have decreased cycling times, and be more efficient and safer. An improved lower pressure reaction vessel that achieves adequate softening, pulverization, and separation of cellulosic fibers with greater efficiency and safety is thus needed.

More specifically, what is needed is an improved reaction vessel that agitates the biomass bearing material to quickly saturate the biomass bearing material with low pressure steam thereby allowing the separation of and collection of a high quality cellulosic fraction from the other fractions of the waste. The vessel should be safe to operate and efficiently use the heat and steam so that the moisture content of the product is low, and provides a sterilization effect upon the biomass bearing material, imparts a chemical change to the biomass bearing material and imparts beneficial handling, flow, and chemical characteristics to the product of processing in the reaction vessel, which thus converts the biomass from waste into a feedstock for subsequent processes. Additionally, the non biomass fractions can benefit by removing labels from containers, fracturing glass for possible later separation from the waste stream, compacting and agglomerating plastics, and compacting ferrous and non-ferrous materials.

SUMMARY OF THE INVENTION

Included with this disclosure are improvements to the disclosures in U.S. patent application Ser. No. 11/355,632 (U.S. Publication No. 2007/01990643, U.S. Pat. No. 7,745,208) and result in an efficient and safe reaction vessel.

The reaction vessel and processes described herein result in the highly efficient and safe separation of the cellulosic fraction from a biomass waste stream. Efficiency is conferred by improvements which result in the use of less process steam to treat the biomass bearing material which thereby: 1) reduces the quantity of vented end-of-process steam and therefore condensate; 2) improves the isolation of recyclable materials by reducing surface tension promoted by excess moisture; 3) extends the shelf life of processed biomass by reducing the moisture content; 4) extends and improves the operational life of the vessel by stabilizing operating conditions; 5) reduces or eliminates the need for post treatment processing, e.g., drying, of the materials for other uses; and 6) reduces contamination of the cellulosic fraction with plastic material and other containments because of the reduced temperatures and pressures. As discussed in greater detail below, improved safety results from the improved door, door sealing system, and insulated heated jacket that each reduce the risk of an operator being injured during use of the vessel.

It will be appreciated that the reaction vessel disclosed herein includes a number of features each of which individually or in various combinations can be useful in the meeting the objectives described above.

The reaction vessel described herein includes a generally cylindrical reaction vessel with a first end and a second end. The vessel is configured to rotate in one direction to load the biomass bearing material through an access opening at one end of the vessel and to pulverize and heat process the material. The rotation of the reaction vessel is reversible to further pulverize and move the biomass bearing material back toward the access opening end for removal of the biomass bearing material through the opening.

The vessel is rotated, such as, through the use of one or more support tracks, wheels, and trunnion assemblies to support the reaction vessel as it rotates. It also has a drive mechanism for powering the rotation of the reaction vessel and its contents. The vessel can be set at different angles from the horizontal, including at about 3 to 10 degrees, or preferably 4 to 8 degrees.

An improvement to the reaction vessel is that it may optionally include a heated jacket that heats the wall of the reaction vessel which in turn heats the biomass bearing material. The heated jacket includes an outer covering and a structure for circulating a heated media, such as steam, around the outer surface of the vessel thereby heating the vessels interior. The heated jacket may optionally be further insulated. The heated jacket unexpectedly increases the operating efficiency of the reaction vessel because is decreases the amount of process steam injected into the vessel to heat the biomass bearing materials inside which results in 1) lower energy consumption during processing due to direct heating of the biomass material, 2) a product with a lower moisture content because less process steam is needed to reach the desired operating pressures, 3) greater efficiency because processing time is decreased due to the material being heated during loading and because the process steam is not being used to heat the vessel wall, and 5) improved safety in vessels with insulated heated jackets because the likelihood of burns caused by incidental contact with the hot outer surface of the reaction vessel is decreased. Also, the heated jacket evenly heats the outer wall of the reaction vessel which decreases eccentricities in the axis of rotation introduced by uneven expansion of the metal reaction vessel which can further improve the efficiency with which the vessel operates. Moreover, the heated jacket improves the ability of the vessel to accurately maintain the desired operating temperatures and pressures which results in more consistent processing of waste materials and in a higher quality product having less contamination.

The reaction vessel includes an access opening through which biomass bearing material may be loaded into and removed from the reaction vessel. The reaction vessel includes a door assembly, which is adjacent to the access opening, for closing the access opening and holding the door closed against pressure from within the vessel. The description of the material to be processed in the vessel is described as biomass bearing material, with the understanding that this refers to any waste or by product stream containing fibrous, cellulosic, or biomass material, including streams otherwise described further as organic, putrescible, municipal solid waste, and including sewer sludge, industrial waste and by product streams, agricultural and food processing streams, and other cellulose or organic bearing streams.

The reaction vessel includes one or more improved flights of auger vanes on the interior wall of the reaction vessel for moving biomass bearing material from the first end to the second end of the vessel. The flights, through rotation of the vessel, cause the biomass bearing material to move from one end of the reaction vessel to the other and back again towards the door opening. The auger vanes have a base edge, which is attached to the interior vessel wall, typically by welding. Of course brackets or studs or other known attachment methods can also be used for this purpose.

The one or more auger vanes also have a top edge defining a bore parallel to the long axis of the reaction vessel. The bore can optionally have a diameter that is approximately one third of the diameter of the reaction vessel, when seen in cross section or end view. This means that the space defined by the auger vanes occupies about two thirds of the cross sectional diameter of the reaction vessel.

The auger vanes can be constructed to be one or more continuous spirals from one end to the other of the reaction vessel. The auger vanes can also be broken into a series of arching vanes, with each section welded or otherwise attached to the interior wall of the reaction vessel and contributing to the auger effect during rotation of the vessel.

A feature of the reaction vessel is a number of raised projections that extend from the top edges of auger vanes. As the reaction vessel turns and biomass bearing material tumbles within the auger vanes, the raised projections on the top edges of the auger vanes aid in moving, pulverizing, and shredding the biomass bearing material. The raised projections may be generally rectangular, trapezoidal, triangular, or rounded in shape, with one edge attached to the auger vane top edge. The top edges of the raised projections form the bore of the reaction vessel, with the bore in some exemplary embodiments having a diameter that is approximately ⅓ the diameter of the reaction vessel when seen in cross-section or end view.

The raised projections can include improved projections that are cupped and are joined to the auger vane or the paddles so that the free edge of the cupped projection is angled toward the access opening. The cupped projections are improvements of the paddle-like projections disclosed in U.S. Publication No. 2007/01990643, incorporated herein. The cupped projection unexpectedly improves the mechanical agitation of the waste by auger of the reaction vessel and serves to fluff the waste and the efficiency with which the vessel is emptied. The increased agitation decreases the operating times and pressures required to separate the cellulosic fraction from the other fractions of the waste stream. In addition, the cupped projections being angled toward the access opening allow for efficient emptying of the vessel. In particular, solid waste streams include some waste materials, such as certain fabrics, metal cables, wires, chains, and hoses that may not be completely broken down during processing. These materials will have an increased propensity to snag on discontinuous raised projections that that are angled to project away from the access opening. However, angling the cupped projections toward the access opening allow these materials to away from the auger vane while at the same time propelling them toward the opening during emptying. Moreover, while the paddle-like projections in U.S. Publication No. 2007/01990643 also decrease snagging of these types of materials, the angle of the cupped projections also imparts significantly greater agitation to the waste materials as the materials are forced over and around the cupped edge during processing.

Some of the raised projections can be in the form of paddles as described in U.S. Publication No. 2007/01990643, which are attached to the top edge of the auger vanes. The paddles may be attached directly to the top edge of the auger vane or may be attached to structures called rods or posts are attached to the top edge of the auger vane and extend toward the interior of the reaction vessel and away from the top edge of the auger vane. The paddles may be generally rectangular in shape. The paddles may be spaced apart from the top edge of the auger vanes and the paddles have a top edge which is closest to the center line of the reaction vessel from the top edge of the auger vane. The paddles extend from the top edge of the auger vane in the same general plane as the auger vane.

Some of the raised projections may be oriented in a plane generally normal to the plane of the auger vane. This results in raised projections perpendicular to the auger vane and parallel to the long axis of the reaction vessel. These projections can point in one or both directions from their attachment point on the auger vane top edge, resulting in jagged teeth pointed backward and forward perpendicular to the general orientation of each auger vane.

The reaction vessel can be considered to have three sections. The first section is adjacent to the access opening. The second section is positioned in the middle of the reaction vessel. The third section is positioned at the end of the reaction vessel opposite the access opening. Locating raised projections, including cupped projections and/or paddles, in the third section of the reaction vessel is advantageous. Thus, a reaction vessel could be built with raised projections, including cupped projections, and/or paddles in the third section, or in the third and second sections, or in all three sections of the reaction vessel.

The biomass bearing material treatment vessel may further include one or more chain sections that are attached to the interior of the vessel that function to supplement the agitation provided by the raised projections. The chains may be attached in various lengths, but typically two to six feet is sufficient to accomplish the purpose, while three to four feet has also proven effective. The chains would be sized according to the size and capacity of the reaction vessel, but a thickness of ¾ inches has proven successful for one preferred embodiment. The chains are attached so that they hang freely in the biomass bearing material treatment vessel. A chain detachably attached to the auger vane about every six feet is a preferred configuration. When the vessel rotates, the chains assist in agitating, pulverizing, and mixing the biomass bearing material contained within the vessel.

The reaction vessel includes a steam injection system by which steam is injected into the vessel via steam longitudinal sparging lines that run along the sides of the reaction vessel parallel to the long axis of the reaction vessel. An improvement to reaction vessel described herein is that the longitudinal steam sparging lines may be coupled to one another within the vessel by one or more circumferential sparging lines that run around the inner circumference of the reaction vessel. The circumferential sparging lines provide additional input of steam that surrounds the waste materials and improves the efficiency with which the materials are saturated with steam. The circumferential sparging lines unexpectedly increase the operating efficiency of the reaction vessel by 1) lower energy consumption during processing due to improved saturation of the biomass material, 2) decreased processing time and correspondingly the cost of operation, 3) producing a product with a lower moisture content because less process steam is needed to saturate the biomass materials, 4) by lowering moisture content which results in decrease post-process drying and improves the efficiency with which other materials are separated from the cellulosic fraction, and 5) improving the quality of the separated cellulosic fraction for use as feedstock for other processes. The steam sparging lines, both longitudinal and circumferential, penetrate the auger vanes where the auger vanes are attached to the vessel wall. The steam sparging lines receive their steam from a circular steam manifold that connects to all of the steam lines. The steam manifold rotates with the vessel and is attached to a rotary joint through which steam is injected into the steam manifold and the vessel. The steam sparging lines can extend the entire length of the vessel and can optionally extend out the end of the vessel opposite from the end in which the steam is injected. The steam sparging lines include orifices through which steam is introduced to the interior of the vessel.

The biomass bearing material treatment vessel may also include an effluent condensation system. Part of the effluent condensation system is a steam eductor. The steam eductor operates on the principal that when air is blown into a cone, it creates a vacuum. In this case, the vacuum pulls the steam, previously injected into the vessel, from the vessel into a condensing chamber where condensation takes place.

The condensation system is achieved by putting the steam from the processor in contact with a cooler media that will cause the steam to cool and condense. The condensing of the steam thus creates a vacuum.

The biomass bearing material treatment vessel includes a door assembly, which is adjacent the access opening. The door assembly includes a door, which covers the access opening, and a support for the door.

As disclosed in U.S. Publication No. 2007/01990643, the door can be convex. An improvement described herein is a concave door. The concave door is made possible due to the lower operating pressures of the reaction vessel. An advantage of the concave door is that the door sealing assembly, described in greater detail below, may be largely incorporated into the door's cavity thus decreasing the amount of the sealing system that extends beyond the circumference of the vessel. This results in a significant safety advance over previously described door sealing assemblies. Specifically, previously described door sealing assemblies were attached to the reaction vessel near the access opening and projected significantly beyond the circumference of the vessel. Thus, as the vessel rotated, the mass of the sealing assembly projecting beyond the circumference of the reaction vessel also rotated which could hit an operator of the vessel, such as during loading, unloading, inspections, etc. An additional advantage of the concave door is that it decreases the overall height of the vessel which in turn decreases required overhead space of the building in which the vessel is housed thereby decreases capital costs.

The davit assembly includes a generally vertical davit upright, which supports the door through a generally horizontal door support arm. The support arm has a first end and a second end with a counterweight attached to the first end and the access opening door attached to the second end. The davit assembly is configured to rotate around the davit upright so the access opening door may be rotated away from or toward the access opening. This can be accomplished by manual rotation of the davit assembly or it can easily be automated.

The door elevating assembly includes at least one arm, which supports the door with an elevating support arm. The door elevating support arm has a first end and a second end. The first end is pivotally coupled to a supporting base located above the access opening of the reaction vessel. The second end is rotatably coupled to the door by a boss. The coupling between the boss and the second end may also include a mounting plate and a support structure that allows the boss to move laterally and horizontally to accommodate eccentricities in the axis of rotation of the reaction vessel. For example, the mounting plate may be coupled to the second end of the elevating support arm with the boss coupled to mounting plate by the support structure. The support structure may include pistons configured to allow horizontal and vertical movement or other such structures such as elastomeric members and/or pivoting members. The elevating assembly is configured so that the elevating support arm pivots about the coupling to the support base allowing the access door to move upward away from the access opening or downward toward the access opening. This can be accomplished by known mechanisms including hydraulic actuators coupled to the elevating support arms. The supporting base may be coupled to a structure suspended over the reaction vessel.

The door sealing system of the vessel includes a first raised locking rim, which surrounds the access opening. This first raised locking rim corresponds with a second raised locking rim, which surrounds the access opening door, which will be referred to as simply the door. When the door is placed adjacent the access opening, the first locking rim is side-by-side with the second locking rim, which is on the door itself. The door sealing system includes a clamp collar for sealing the two locking rims together. Thus, it holds the access opening door over the access opening. The clamp collar can further include a first section and a second section with one or more joining devices for joining the two sections together. The joining devices can be one or more clamp screws that draw the first and second clamp sections and thus hold them together until released. The clamp screws move through threaded bosses on the sides of the clamp collar sections. The door closing assembly can comprise two clamp screws, which are mounted on corresponding bosses on the sides of the first and second clamp sections. The clamp screws are driven by one or more motors such that the collar sections may be pulled together or pushed apart through the use of threaded screws. As described above, the door sealing assembly may be attached to the door such that the clamp screw motors and clamp screws are located at least partially in the cavity of the concave door thereby limiting the extent to which the door sealing system has components that rotate outside of the diameter of the reaction vessel thereby improving safety by decreasing the risk that an operator will be struck by a rotating component of the assembly.

The first and second locking rim can each include a contact surface and an outer bevel, and, optionally, one or both of the contact surfaces may include a seal, such as an O-ring in a groove, a gasket, etc. The outer bevel surface on the first locking rim is located on the side opposite the contact surfaces of the locking rims. The outer bevel surface on the second locking rim is also on the side of the locking rim away from the contact surface. The clamp collar sections include inner angled surfaces that correspond and interact with the outer bevels of the first and second locking rims and function to hold the door in the closed position during operation. As the clamp collar sections close on the locking rims, the inner angled surfaces of the clamp collar sections interact with the outer bevels of the first and second locking rims to guide the door into alignment with the access opening.

In an improved embodiment of the door locking system, at least one of the contact surfaces of the locking rims also includes an angled surface that assists in aligning the doors. For example, the contact surface of one locking rim is angled and the contact surface of the corresponding contact surface is beveled such that as the clamp collar section interact with the outer bevels, the angled and beveled contact surfaces of the locking rims guides the door into alignment over the access opening. The angled and beveled surfaces may be on either of the first and second locking rims so long as they are configured to guide the door into alignment over the access opening.

The angled and beveled contact surfaces improve on the accuracy with which the door is aligned with the access opening. Improving the accuracy of the alignment improves the seal formed between the door and the vessel, results in less stress being transferred to the door support systems during operation than when the door is not accurately aligned, and allows the door to be closed and sealed more quickly thereby decreasing the process time and increasing operating efficiency. If the door is not properly aligned and the seal is not formed then the efficiency of the vessel is greatly reduced because a larger volume of process steam will be required to maintain the operating pressures. Thus, improvements to the door that assist in aligning the door provide a significant improvement over older devices.

The biomass bearing material is loaded into the reaction vessel and moved away from the access opening through rotation of the reaction vessel and its auger vanes. When sufficient biomass bearing material is loaded into the reaction vessel, the ambient atmosphere inside the vessel is purged by steam from the sparging lines. When the ambient air is evacuated, the vessel is sealed and the pressure buildup begins as the reaction vessel is charged with steam, i.e., steam is injected into the reaction vessel and heat and pressure builds up to the operating pressure. In one embodiment, the vessel is fully charged in a shortened period of time as compared to older methods, such as in less than about 30 minutes or less than about 15 minutes. Quick charging the vessel with steam reduces the operating time for the vessel and decreases the moisture content of the materials by decreasing the amount of condensation that occurs prior to full charging. Moreover, quick charging the vessel with steam results in greater fracturing of the cellulosic material, a greater yield of the cellulosic fraction, and a higher quality end product with lower contamination from plastic material and other contaminates. High quality biomass output has an increased likelihood of being suitable for use as a feedstock in industries with stringent regulatory controls. For example, under various regulatory guidelines, contamination with plastic materials can prevent the biomass output from being certified as a renewable energy source, such as for direct combustion or as a feedstock for gasification or fermentation processes. The present process results in a higher quality biomass output that is more likely to pass regulatory muster. This is in contrast to older processes that utilize longer charging times thereby result in longer exposure to wet lower quality steam and yield a biomass output with greater contamination.

Quick charging the vessel may be accomplished using a steam charging chamber capable of quickly providing a large volume of process steam. The steam charging chamber amplifies steam generated in a boiler thereby significantly decreasing the size of the boiler required to operate the vessel. Additionally, during charging with a boiler, the boiler dumps its steam into the reaction vessel which causes the boiler to experience a rapid change in pressure. Rapid pressure changes can fatigue the boiler thereby reducing its service life. In contrast, when using a steam charging chamber, boiler steam is used to heat the water in the chamber and then a smaller amount of steam is dumped into the chamber causing the steam to rapidly expand in the chamber without having to dump all the steam from the boiler. Thus the boiler avoids the rapid changes in pressure. Thus, the steam charging chamber decreases capital investment in a larger boiler, improves the service life of the boiler, and by providing a rapid charge of steam, decreases the cycle time for processing the materials.

An internal operating pressure of less than 15 p.s.i.g. has been found to be suitable for the purposes of this method and provides the additional advantage in that the vessel is not be required to be classified as a pressure vessel. However, use of higher steam pressures such as high as 55 p.s.i.g. is also a possible variation of the process. The reaction vessel is rotated, while steam is injected for a period of time to soften the fibers of cellulosic waste within the biomass bearing material. Steam is injected through the steam sparging lines in the vessel. Although the method can operate under varied conditions depending on the particular blend of biomass bearing material being treated, a reaction time of approximately fifteen to forty-five minutes has been found to be sufficient to soften the fibers of most biomass bearing material and to achieve good sterilization. However, the improvements to the reaction vessel described herein allow for significantly shorter processing times than was previously possible. After this time has been reached and sufficient time has been allowed for churning, shredding, and pulverizing the biomass bearing material, the steam is evacuated through the use of a steam eductor system. The steam eductor system includes an air nozzle and operates by airflow through an orifice that creates a vacuum.

The internal atmosphere from the vessel is thus removed through a barometric condenser before the vessel is opened in order to reduce the volume of escaping emissions from the vessel. After evacuation is accomplished, the door is removed and the processed material, hereinafter called feedstock material, is removed by rotation of the vessel and propelled by the action of the auger vanes. The feedstock material at this point has been chemically altered and is no longer biomass bearing material in terms of chemistry or physical characteristics. As feedstock, it is ready for use in any number of operations which require a cellulose or carbon based feedstock. After being removed from the reaction vessel, the feedstock material is treated for separation of the cellulosic fiber components from other materials such as plastic, aluminum, glass, and various metal components. The separation processes that are well known in the industry separate each of these streams, which is the subject matter of other patents and practices.

Another aspect of the invention is a feedstock and a process for making a feedstock for other operations, the feedstock being made from the vessel of the invention. After processing in the vessel the feedstock material is chemically and physically different than the biomass bearing material which was placed in the reaction vessel, and is a superior feedstock for many applications including as a bio-energy product of various kinds. The feedstock material is a superior feedstock for processes that convert fibrous materials into a liquid, solid or gaseous bioenergy product and can be further subjected to other processes or treatments for production of similar or subsequent products and can be further subjected to other process or treatments for production of similar or subsequent products. The change in the biomass bearing material into a feedstock is due to a chemical reaction of the cellulosic portion of the feedstock material in the reaction vessel, and is not just a separation process. In this reaction, the cellulose and hemicellulose molecules of the fibrous portion of the feedstock material are broken down and formed into simpler compounds. These compounds have less crystallinity than the original cellulose and hemicellulose constituents of the fibers.

Because of an increased surface area and homogenous sizing caused by the novel process, the feedstock may be efficiently used for use in gasification. The produced gas can be utilized as a substitute for natural gas or can be compressed or liquefied. The produced gas, or "syngas", could also be stripped of various elements, including hydrogen. The syngas can also be converted by other methods into ethanol, "bio oils" and other chemicals or energy sources. Alternatively, the feedstock can be used in the process of hydrolysis, whereby the feedstock is used to produce sugars for distillation and other uses. The feedstock can also serve in a solid energy product, in which free flowing solids or pelletized or granular feed are burned for energy Another process for which the feedstock material of the invention is suitable is as furnish. Furnish is a fibrous product which is used as a feedstock in the paper industry. Furnish is fed into the paper making process and also used to make insulation, absorbents, corrugation, fireproofing, and many other pulp products.

Still other features and advantages of the present invention will become readily apparent to those skilled in this art from the following detailed description describing certain embodiments of the invention, simply by way of illustration of the best mode contemplated of carrying out the invention. Moreover, each of the various components can be used individually or in various combinations. As will be realized, the invention is capable of modification in various obvious respects all without departing from the invention. Accordingly, the drawings and description of the certain embodiments are to be regarded as illustrative in nature, and not as restrictive in nature.

DETAILED DESCRIPTION OF THE INVENTION

Figure 1:
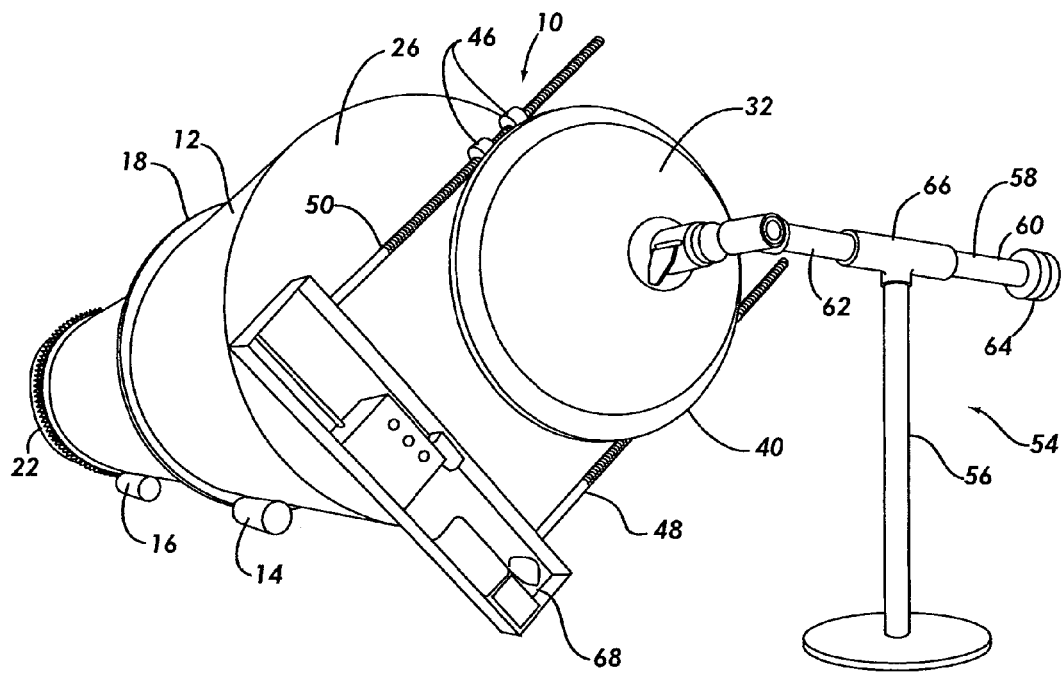
FIG. 1 is a perspective view of the Biomass bearing material processing vessel.

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

Some of the preferred embodiments are shown in the FIGS. 1 through 24. FIG. 1 shows the biomass bearing material treatment vessel 10. It includes a reaction vessel 12. In one mode of the invention, a first trunnion assembly 14 and a second trunnion assembly 16 supports the reaction vessel 12. The trunnion assembly includes a track 18 and a trunnion 20. These components can be sized according to the size of a specific reaction vessel. However, in a preferred embodiment of the vessel, the trunnions are cylinders of solid steel approximately fifteen inches in diameter and approximately ten inches in length. The vessel 10 is preferably tilted at an angle, and may be configured to have an adjustable angle. For fixed angle versions, an angle from 2 to 10 degrees is preferred. More specifically, an angle of 4 to 8 degrees is desirable, and an angle of approximately 6 degrees is optimal.

The reaction vessel also includes a gear ring 76 around its outer circumference, which is driven by a motor 80 and a drive gear 78. In one embodiment of the gear ring 78 is approximately ten inches wide and is made of steel approximately five inches thick. While a geared drive system is shown, other drive systems would also work, including a chain and sprocket drive, a belt drive, a wheel drive, or a cradle formed by a chain and sprocket under the vessel.

The reaction vessel 12 can take a number of configurations with different sizes depending upon the desired capacity and throughput of the operation. An exemplary configuration of the reaction vessel is approximately fifty feet long and ten feet in diameter. It is made generally of one-half inch steel plate with one and one-fourth inch reinforced steel plate in the region of the trunnion assemblies 14, 16 and the track 18. The exemplary reaction vessel has a rounded ellipsoidal head at the second end 22 of the reaction vessel. At the first end 24 of the exemplary reaction vessel, the vessel tapers from approximately a ten foot diameter to approximately a six foot diameter opening on a frustoconical section approximately five feet in length. A cylindrical collar 28 with a first locking rim 30 is at the narrow end of the frustoconical section 26. Shown adjacent the first locking rim 30 in FIG. 1 is the door 32, which includes a second locking rim 34.

Figure 13:
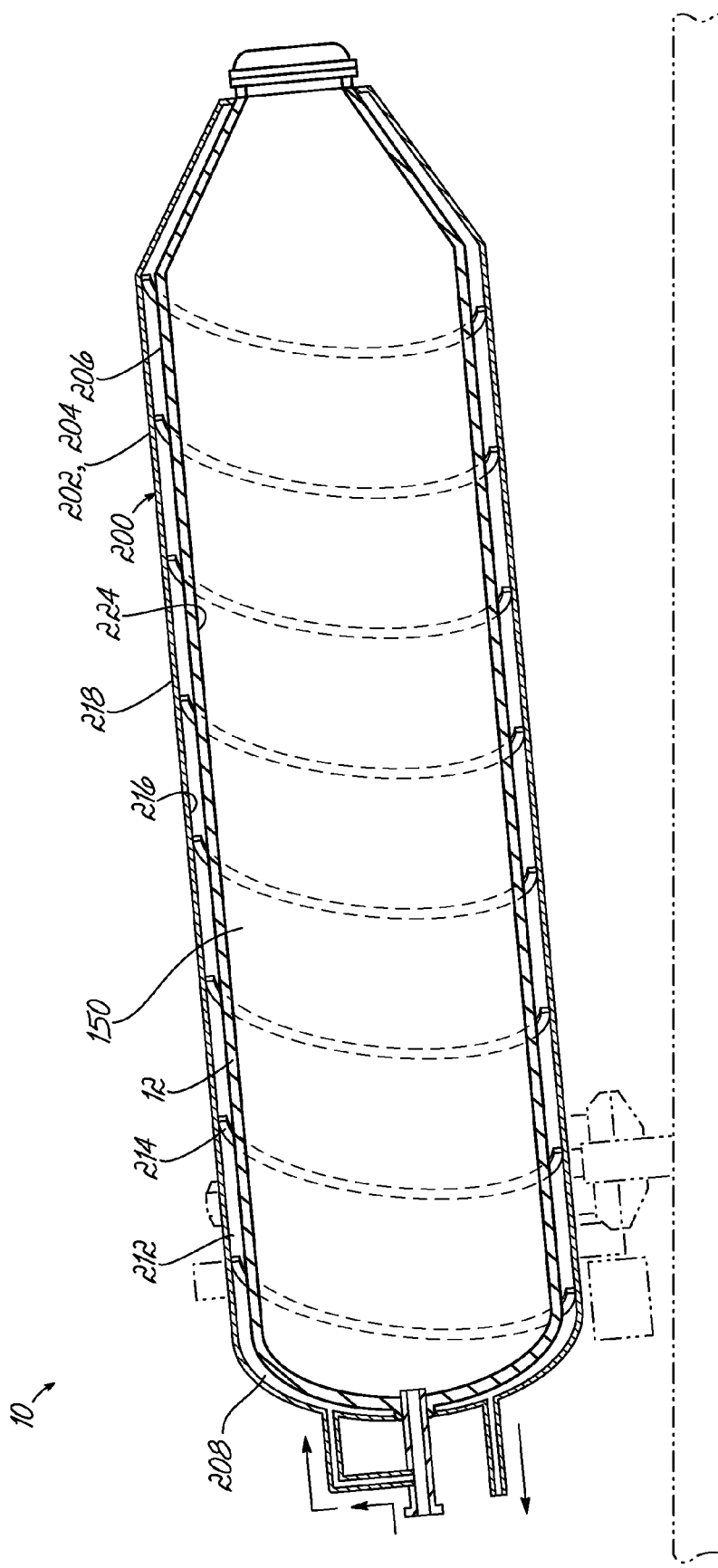
FIG. 13 is cross-sectional view of a reaction vessel with a heated jacket.

The reaction vessel may optionally include a heated jacket 200 surrounding reaction vessel's outer surface (FIG. 13). The heated jacket 200 includes an outer covering 202 such as a sleeve 204 that envelopes at least a portion of the outer surface 206 of the reaction vessel 12 and a structure 208 for circulating the heated media. The outer covering 202 can be, for example, a steel sleeve that fits over the length of the reaction vessel 12. The heated media circulating structure 208 includes a channel 212 such as created by tubing (not shown) or between the outer covering 202 and/or a series of vanes 214 extending between the outer surface 206 the reaction vessel 12 and the internal surface 216 outer covering 202 that directs the heated media in a course around the vessel 12. For example, the vanes 214 could be attached to the outer surface 206 of the vessel 12 and/or the inner surface 216 of the sleeve 204 (or both) to form a channel 212 that wraps around the vessel 12 from one end to the other and back. The circulating structure 208 is in fluid communication with a supply of the heated media, such as a boiler (not shown). In one embodiment, the circulating structure 208 is connected to the heated media supply by a rotary joint, such as rotary joint 84. The heated media could include heated liquids and gases such as oil or steam. In embodiments wherein the heated media is steam, the steam could be supplied by the sparger manifold 82. The heated jacket 200 may optionally be further insulated (not shown) to prevent the loss of heat. For example, the heated jacket may include a layer of foam insulation on its outer surface 218.

The heated jacket 200 operates in addition to and augments the heat and steam introduced into the interior 150 of the reaction vessel 12 by the longitudinal 88 and circumferential 280 sparging lines. The heated jacket 200 functions to reduce the amount of moisture in the unprocessed mass inside the reaction vessel by contact and radiant heating, resulting in: 1) less process steam being used to heat the vessel wall and unprocessed mass; 2) reducing the quantity of vented end-of-process steam and therefore condensate; 3) improving the isolation of recyclable materials by reducing surface tension promoted by excess moisture; 4) extending the shelf life of processed biomass by reducing the moisture content; 5) extending and improving the operational life of the vessel by stabilizing operating conditions; 6) reducing or eliminating the need for post treatment processing, e.g., drying, of the materials for other uses; 7) when insulated, improving safety by reducing the risk of contacting the heated surface of the vessel; and 8) reduce contamination of the product with plastic material and other containments because of the reduced temperatures and pressures that are made possible with this vessel.

Figure 7:
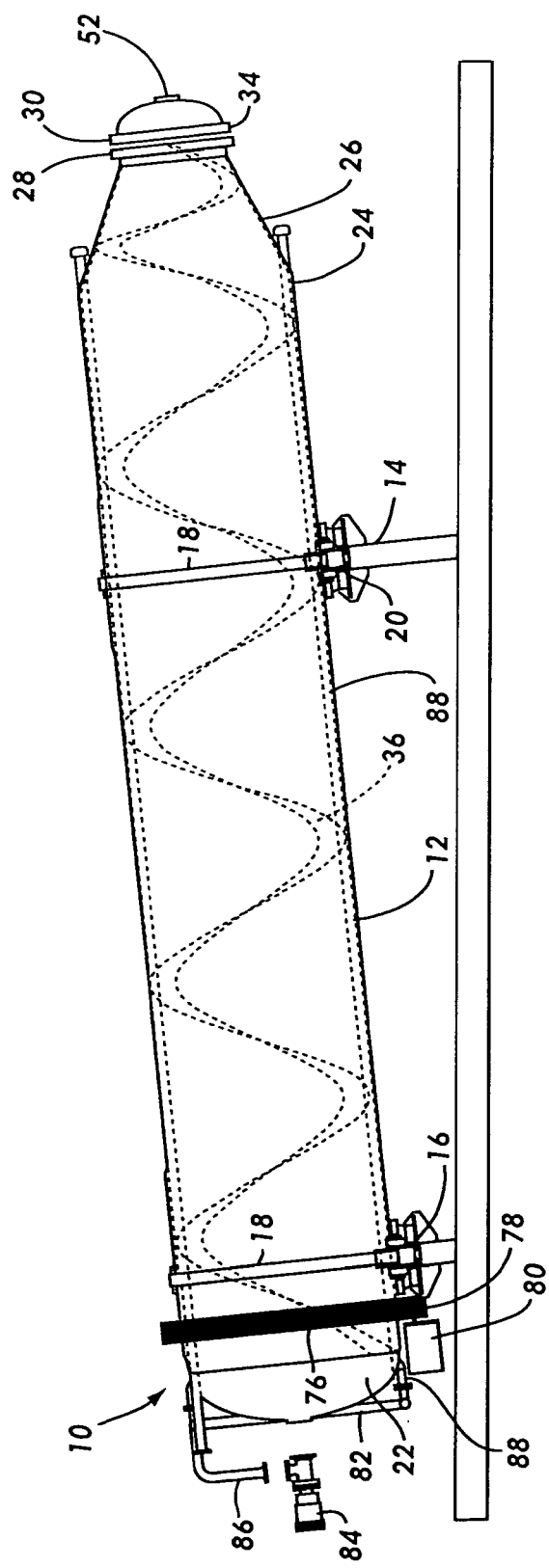
FIG. 7 is an elevation view of the reaction vessel.

A spiraling auger vane 36 is located inside 150 the reaction vessel 12. In one exemplary embodiment, the auger vane 36 is made of three eights inch thick steel, welded at its base edge to the interior of the reaction vessel wall. The top edge 72 of the auger vane 36 extends away from the inner surface 224 reaction vessel wall towards the center of the reaction vessel 12. Although the exemplary auger vane 36 is shown in FIG. 7 as being one continuous spiral from the first end 24 to the second end 22, the auger vane 36 could also be constructed of multiple spirals or several disconnected sections, which together form a spiraling configuration attached to the inside wall of the reaction vessel 12. The auger vane 36 can be attached to the interior vessel walls 224 by welding or by attachment to brackets mounted to the interior vessel wall 224, or by other conventional means of attachment. Mounting by brackets would allow easier replacement of the vane sections.

Figure 2:
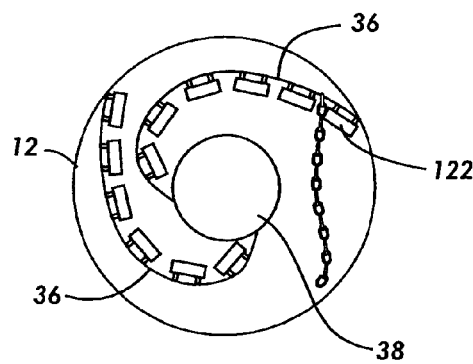
FIG. 2 is a cross-sectional view of the second end of the Biomass bearing material processing vessel.

In one embodiment of the present invention, the auger vane 36 extends into the interior of the reaction vessel 12 and the top edge 72 form the outline of a bore 38. The diameter of the bore 38 in this exemplary embodiment is approximately one-third of the diameter of the reaction vessel 12 of a particular cross section of the reaction vessel 12. FIG. 2 shows such a cross section of a reaction vessel with the bore 38 being approximately one-third the diameter of the vessel 10.

A feature of the reaction vessel 12 is a plurality of raised projections 230 that extend from the top edge 72 of the auger vane 36, as shown in FIGS. 2, 5, 12, 13 and 14. The raised projections 230 may be generally rectangular, trapezoidal, triangular, or rounded in shape. The raise projections 230 can be curved or straight and extend vertically and/or horizontally from the top edge of the auger vanes.

Figure 14:
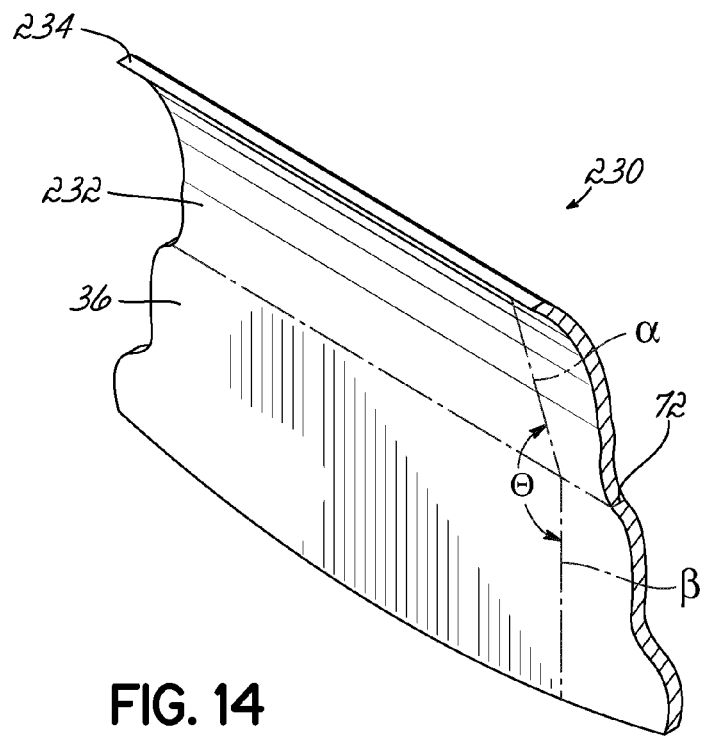
FIG. 14 is a perspective view of an auger vane with a cupped projection.
Figure 15:
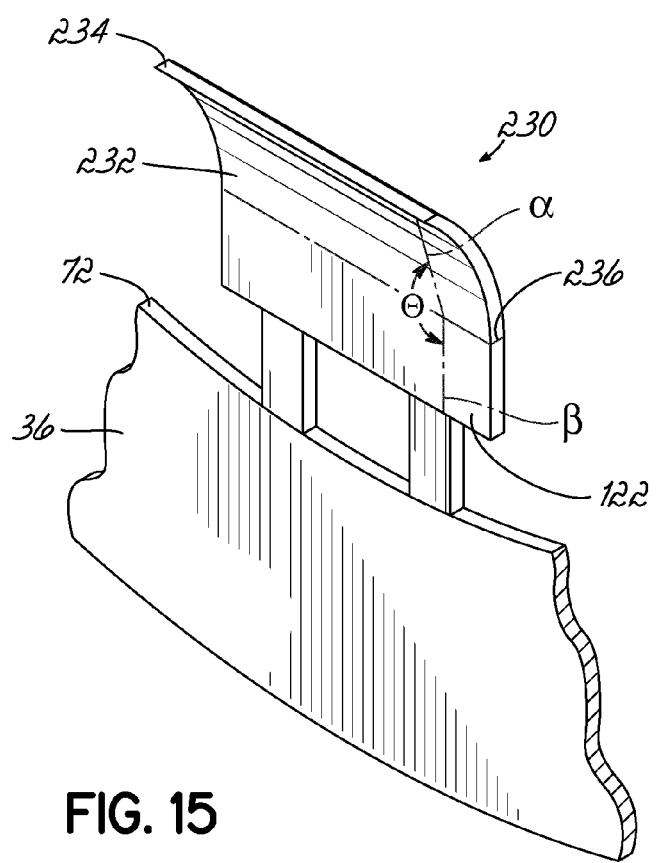
FIG. 15 is a perspective view of an auger vane with a cupped projection on a paddle.

As shown in FIGS. 14 and 15, the raised projections 230 can include improved projections 232 that are cupped so that the free edge 234 angles toward the access opening 52 and are useful in moving the material toward the access opening during emptying and providing an agitating action during processing. In one embodiment, the cupped projection 232 is attached directly to the top edge 72 of the auger vane 36. In another embodiment, the cupped projection 232 is attached to a top edge 232 of the paddle 122. The cupped projection 232 may be continuous or discontinuous over a portion of the auger vane 36. In one embodiment, the plurality of cupped projections 232 is located third of the reaction vessel closest to the access opening 52.

When viewed from the end, the cupped projection 232 may be curved or angled toward the access opening 52. In one embodiment, the cupped projection 232 forms an angle ($\Theta$) with the plane of the auger vane 36. The angle is measured between a first line (or) corresponding with the cupped projection 232 and a second line (B) corresponding generally with the plane of the auger vane 36. In embodiments where the cupped projection 232 is not planer, i.e., is curved or includes multiple angles, the first line 232 (or) is defined by two points wherein the first point is located at the free edge 234 of the cupped projection and the second point is located that the point of intersection with either the auger vane 36 or the paddle 122. In one embodiment, the angle ($\Theta$) is in a range between about 90° and less than 180°, or between about 100° and less than 180°, or between about 120° and less than 180°, or between about 140° and less than 180°, or between about 160° and less than about 180°, or between about 135° and about 150°.

The cupped projection 232 may be formed by, for example, cutting from a rolled section of material, cutting sections from a slit pipe, and bending a sheet of material. The cupped projection 232 may be attached or joined to the top edge 72 of the auger vane 36 or the top edge 236 of the paddle 122 by conventional means of attachment including welding, and attachment with brackets. It is also understood that in the context of the cupped projection 232, the terms attached or joined includes cupped projections 232 that are produced integral with the auger vane 36 and/or paddle 122, i.e. the cupped projection and auger vane, or cupped projection and paddle, are formed from the same section of material. In this case, the point used to determine the angle of the auger vane is the point of transition between the auger vane 36 and the cupped projection 232. The point of transition is the point in which the cupped projection 232 is no longer in the same general plane as the auger vane 36 or the paddle 122.

Figure 12:
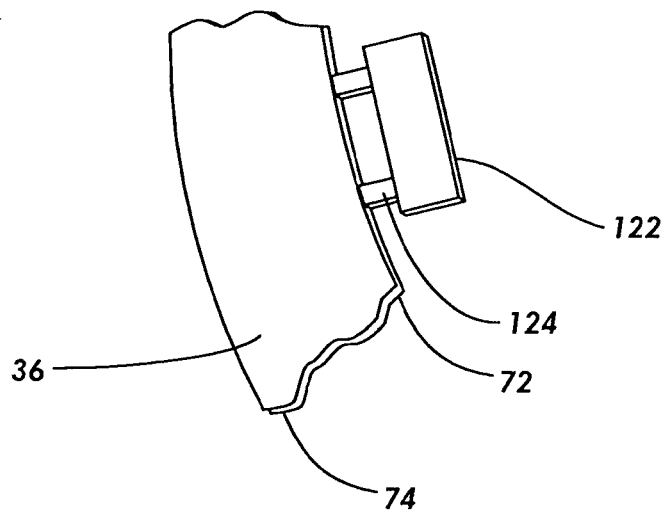
FIG. 12 is a perspective view of an auger vane with paddle.

The raised projections 230 can take another form, as shown in FIGS. 2 and 12, in which the auger vanes 36 has shorter vanes to which are attached paddles 122. The paddles 122 may be joined directly to the auger vanes 36 or optionally, attached by posts 124. The size of the paddles 122 and the optional posts 124 could take many configurations depending on the size of the vessel being built. In the case of a reaction vessel, which is approximately 50 feet long, the vanes and paddles, could be constructed using paddles which are approximately 18 inches wide and 60 inches long, attached by posts 124 which are approximately 24 inches long. The paddles 122 can also form a widened region of the auger vanes 36 and thus extend directly from the auger vane. If placed on the posts 124, the paddles 122 would be spaced apart from the top edge 72 of the auger. The top edge 236 of the paddle 122 would form the periphery of the bore inside the vessel as shown in FIG. 2.

Figure 5:
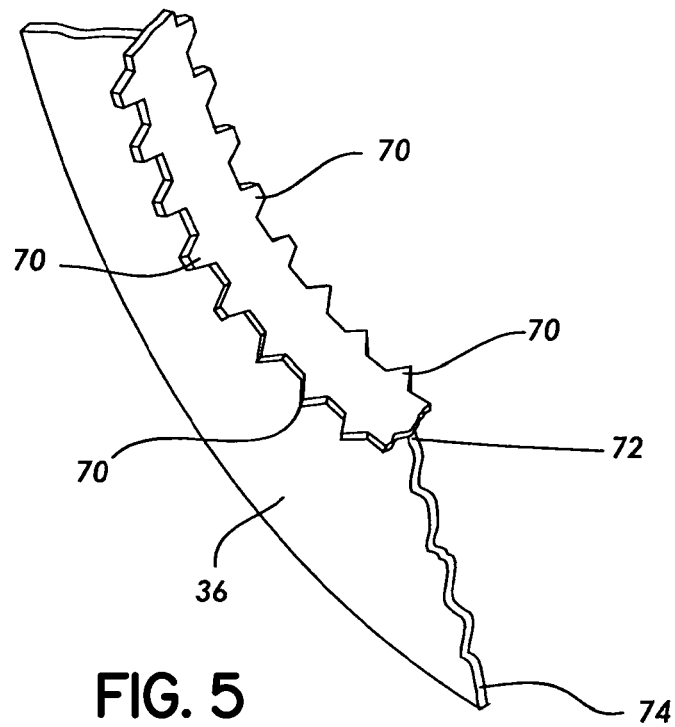
FIG. 5 is a perspective view of an auger vane with projections.

Some raised projections 230 may extend in both directions perpendicular from the auger vanes 36. Such projections 70 can be triangular, trapezoidal or other shapes to form a jagged cutting edge. The perpendicular raised projections should only extend a short distance, such as approximately one inch, from the auger vane 36 to which they are attached so as to prevent snagging of material in the reaction during emptying. In an exemplary embodiment, the perpendicular projections 70 are approximately one to two inches across at the base and are approximately one-quarter inch thick steel welded to the edge of the auger vanes. FIG. 5 shows perpendicular projections 70 attached to the auger vane edge 72 of the auger vane 36. FIG. 5 shows a perspective view of a section of auger vane 36. Attached to this section of auger vane 36 are a number of perpendicular projections 70 that are joined together as a unit and mounted to top edge 72 of the auger vane 36. The base edge 74 of the auger vane is welded to the interior wall of the reaction vessel 12. As the auger vane turns, biomass bearing material is pushed against the auger vane 36 and the perpendicular projection 70 and tumbled from one section of the reaction vessel 12 to another. This allows the perpendicular projections 70 to help shred and pulverize the biomass bearing material.

Figure 8:
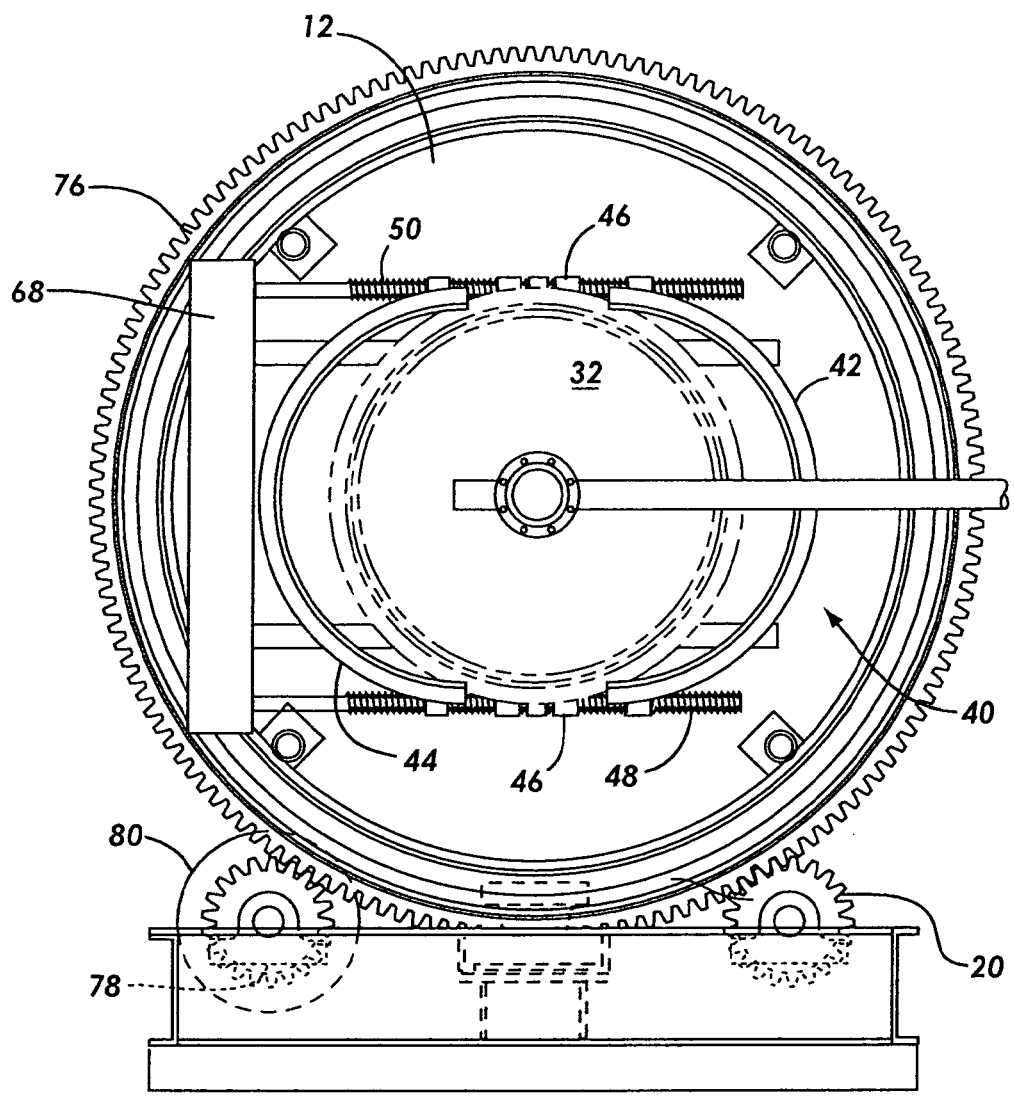
FIG. 8 is an end view of the reaction vessel.
Figure 16:
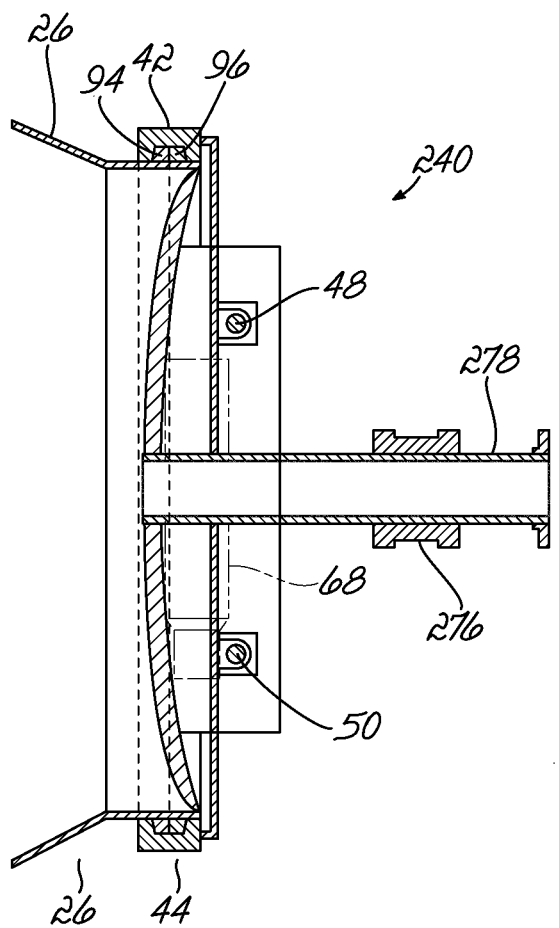
FIG. 16 is cross-sectional view of a concave door with door sealing system.
Figure 17:
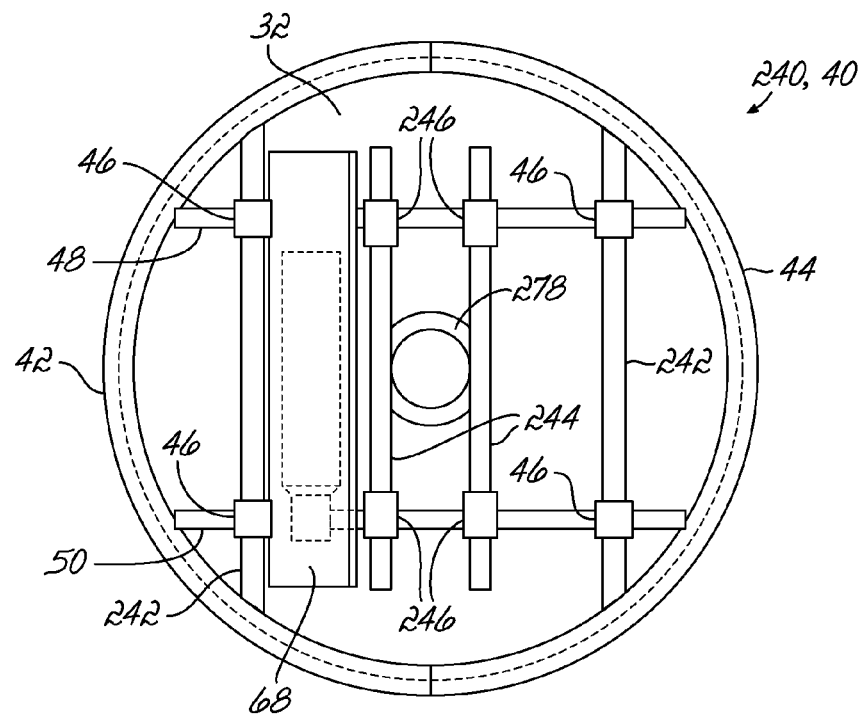
FIG. 17 is front view of a concave door with a door sealing system in the open position.
Figure 18:
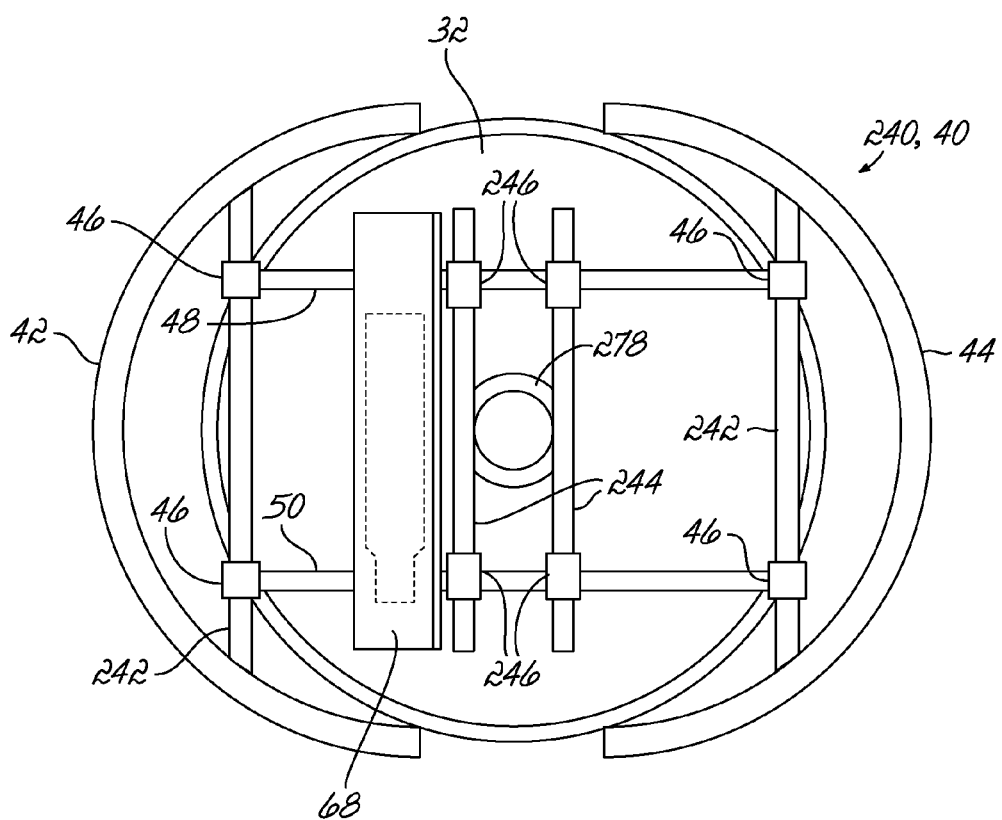
FIG. 18 is front view of a concave door with a door sealing system in the sealed position.

FIGS. 1, 3, 4, 7, 8, and 16-18 show the door 32 of the vessel. In one embodiment, the door 32 is approximately six feet in diameter and, as shown in FIG. 7, is ellipsoidal in cross sectional shape, or as shown in FIG. 16-18, is concave. The door 32 includes the second locking rim 34. The door 32 is sealed to the access opening by the door sealing assembly 240 that includes a clamp collar 40. In one embodiment, the clamp collar 40 is made of a semicircular first section 42 and a semicircular second section 44. However, it is contemplated that more than two clamp collar sections could be employed. Each clamp collar section 42, 44 is coupled to at least one threaded boss 46. For example, the threaded boss 46 may be directly attached to the collar section 42, 44 as shown in FIG. 8 or may be attached to a cross member 242 that is attached to the collar section 42, 44 as shown in FIGS. 16-18. The exemplary embodiment illustrated herein include two threaded bosses 46 with each clamp collar section 42, 44 which correspond with the threaded bosses 46 on the opposite clamp collar section. A first and second clamp collar screw 48 and 50 pass through the threaded bosses 46. The first and second clamp collar screws 48, 50 may be coupled to the door 32 by one or more clamp collar screw cross members 244 using, for example, a pillar block bearing 246 that engages a widened section of the screws. When the screws 48, 50 are turned, such as by one or motors located in a motor housing 68, the pillar block bearings 246 anchor the clamp collar screws 48, 50 allowing the first and second sections 42, 44 of the clamp collar 40 to be drawn together. This locks and seals the door 32 to the access opening 52 of the reaction vessel 10. FIGS. 9, 10, 17, and 18 show this closing operation more closely. In an exemplary embodiment of the invention, the clamp collar screws 48, 50 are approximately one and one-fourth inches in diameter and approximately twenty-five inches in length.

In one embodiment, the clamp collar 40 is coupled, either directly or indirectly to the reaction vessel 12 such that the clamp collar 40 is part of the reaction vessel 12. In another embodiment shown in FIGS. 16-18, the clamp collar 40 is coupled, either directly or indirectly to the door 32 such that the clamp collar 40 is part of the door 32 of the reaction vessel 12. In this configuration, the clamp collar 40 moves in conjunction with the door 32 toward to away from the reaction vessel 12 as the door moves between the closed and open positions. As shown in FIGS. 16-18, and described in greater detail below, door 32 may be concave and can accommodate at least a portion of the door sealing assembly, such as the motor housing 68 and a coupling for the clamp collar screws 48, 50 within the cavity.

FIGS. 9, 10, 19 and 20 show a cross sectional side view of embodiments of the door sealing assembly 240 useful with the reaction vessel. Shown is a portion of frustoconical section 26 and cylindrical collar 28 of the reaction vessel. The first clamp collar section 42 is also shown. Also shown is the first locking rim 30 and the second locking rim 34, which are attached to the door 32. The locking rims 30, 34 have contact surfaces 250 and 252 and outer beveled surfaces 94. The contact surfaces 250, 252 are configured so as to be parallel to one another and to allow the first and second locking rims 30, 34 to contact one another to form a seal therebetween. In the exemplary embodiment shown in FIGS. 9 and 10, the contact surfaces 250, 252 are perpendicular to the axis of the reaction vessel 12. In another exemplary embodiment shown in FIGS. 19 and 20, the contact surfaces 250, 252 are set at complimentary angles with the reaction vessel 12 such that one contact surface forms 250 a beveled surface and the other contact surface forms a corresponding angled surface 252. The complimentary angles of the beveled and angled contact surfaces 250, 252 assist in guiding the door 32 into alignment over the access opening 52. The contact surfaces 250, 252 may also include a sealing material such as a gasket 90 or o-ring. The sealing material may be located in a recess 92 in the contact surface of at least one of the locking rims, such as is shown in the second locking rim 34.

Figure 9:
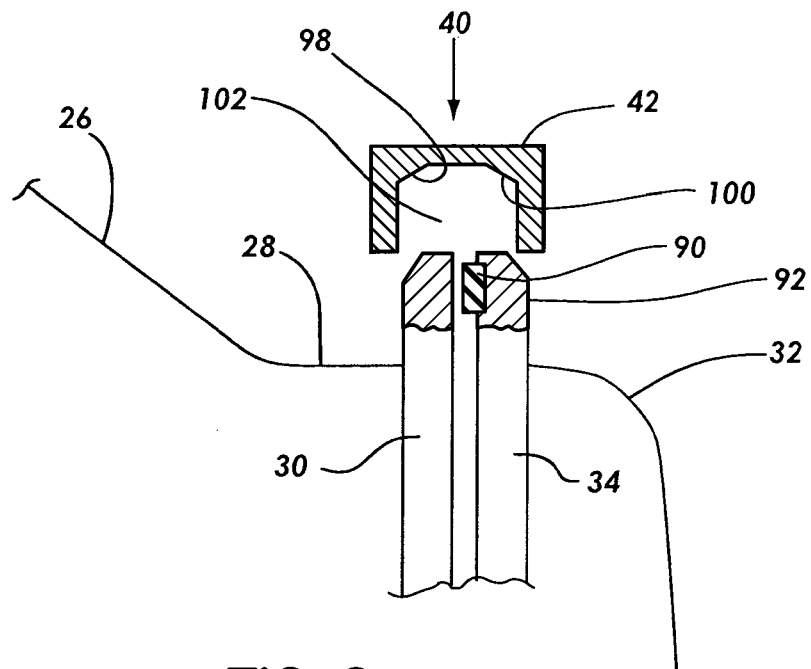
FIG. 9 is a partial cross-sectional view of the closing action of the door assembly.
Figure 10:
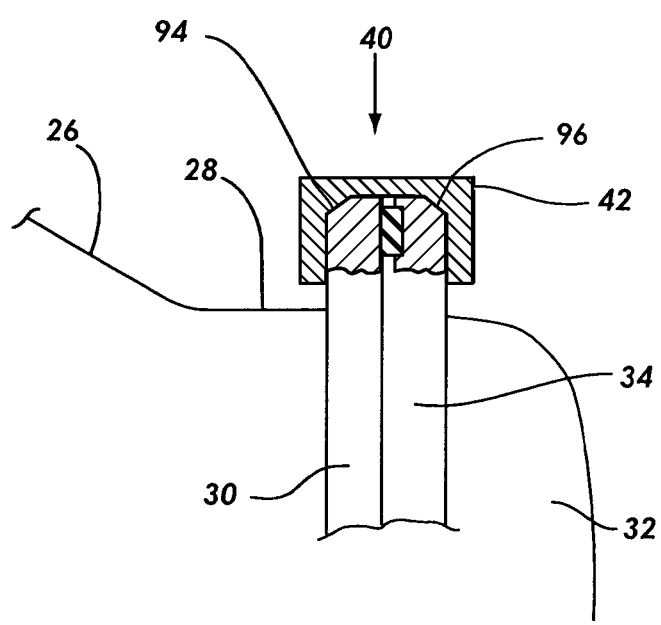
FIG. 10 is a partial cross-sectional view of the door closed against the access opening.
Figure 19:
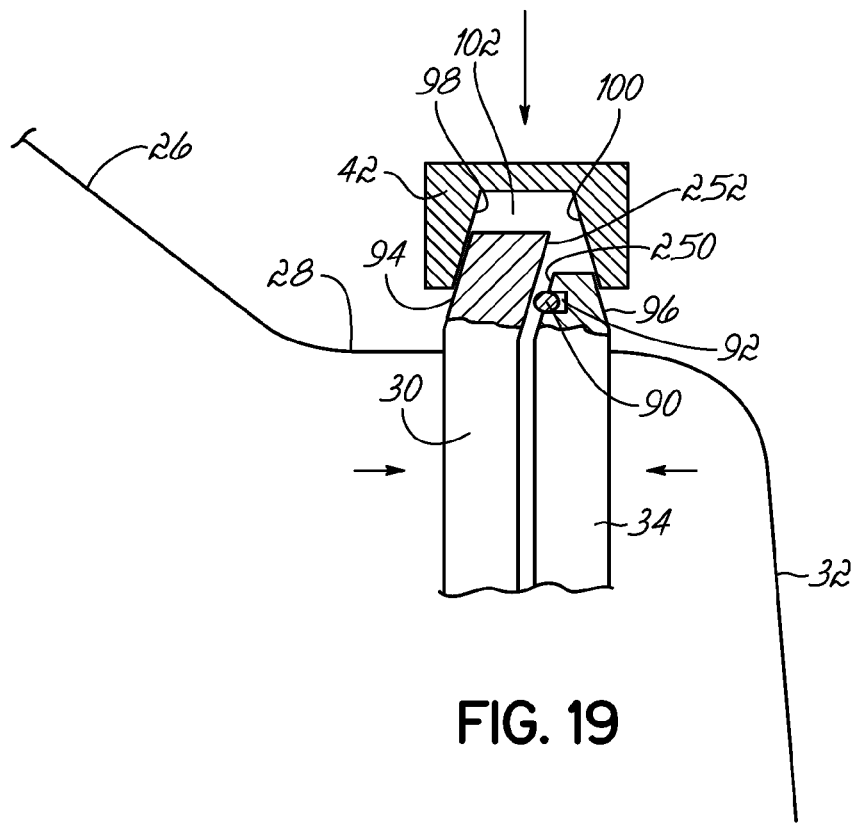
FIG. 19 is partial cross-sectional view of an embodiment of the door sealing system in the unsealed position.
Figure 20:
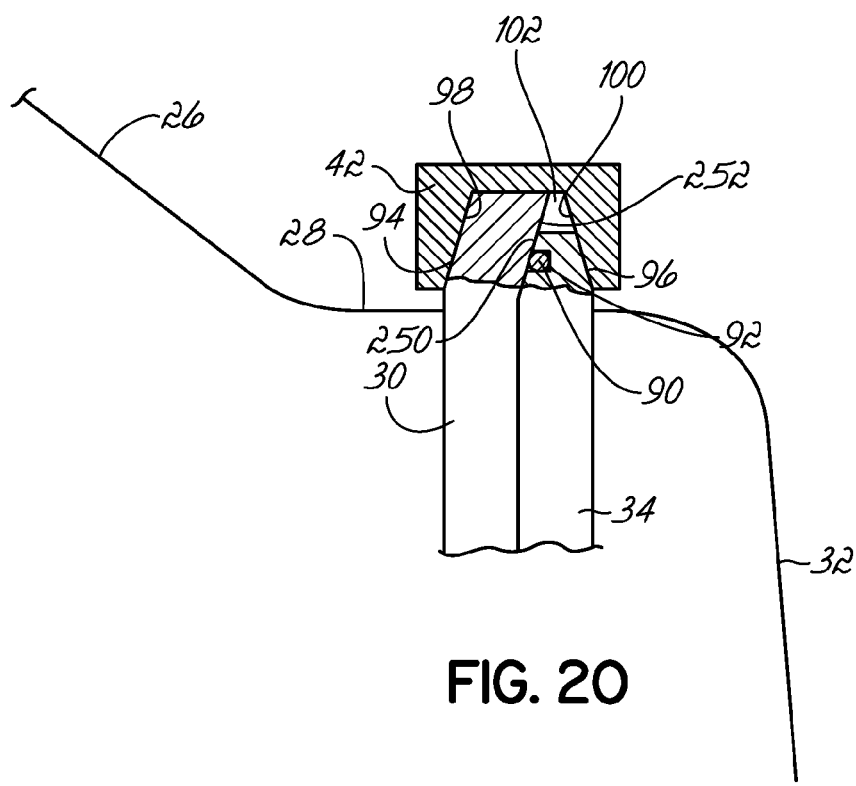
FIG. 20 is partial cross-sectional view of an embodiment of the door sealing system in the sealed position.

As shown in FIGS. 9 and 19, the door 32 is adjacent to but not sealed against the first locking rim 30. The first section clamp collar 42 is adjacent to but not engaged with the first and second locking rims 30 and 34. A second section clamp collar would be similarly positioned (not shown). As the first section 42 of the clamp collar moves down and around the first and second locking rims 30 and 34, it moves into the configuration shown in FIGS. 10 and 20. In FIGS. 10 and 20, the first section clamp collar 42 has moved into engagement with the first locking rim 30 and the second locking rim 34. The outer beveled surface 94 of the first locking rim 30 and outer bevel surface 96 of the second locking rim 34 assist in aligning the door over the access opening. In the position shown in FIGS. 10 and 20, the clamp collar has forced the two locking rims together and holds them together in a sealed configuration. The outer bevel surfaces 94, 96 interact with corresponding angled surfaces 98, 100 in the interior channel 102 of the first clamp collar 42. Although only one clamp collar is shown, it is to be understood that some embodiments utilizes at least two semicircular clamp collars which bring the door into sealed engagement with the access opening as shown in FIGS. 9, 10, 19 and 20. It is further understood that a single ring clamp collar (not shown) could also be used and function as described above.

Figure 3:
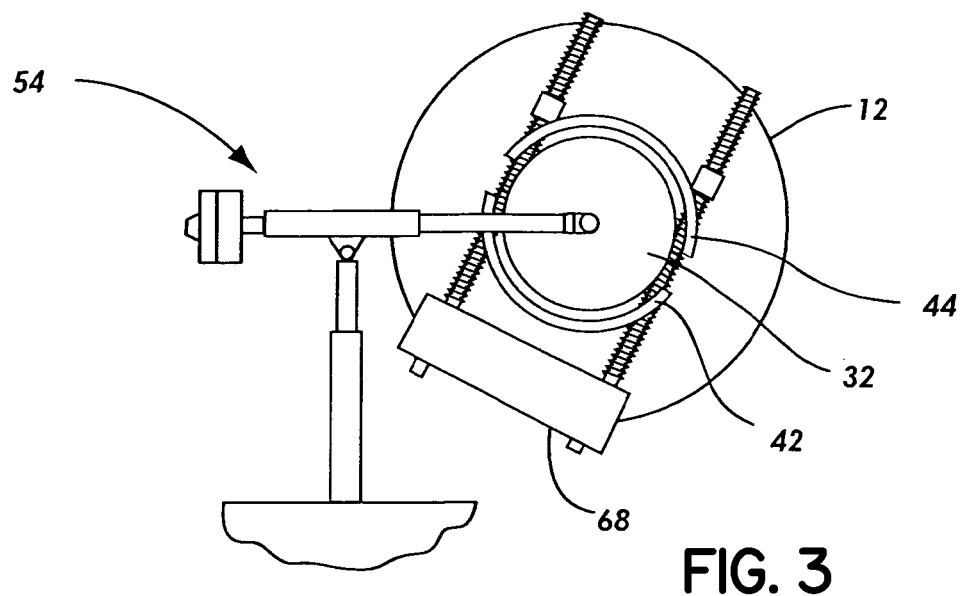
FIG. 3 is front view of the davit and door assembly.

FIGS. 3 and 18 shows a front view of the door 32 with the first section clamp collar 42 and the second section clamp collar 44 are in the open position, so that the door 32 may move away from the access opening 52.

An embodiment of the invention includes a davit assembly 54, as shown in FIG. 1. The davit assembly 54 includes a davit upright 56 and a door support arm 58 with a first end 60 and a second end 62. A counterweight 64 is attached to the first end 60 of the door support arm 58. The door 32 is attached to the second end 62 of the door support arm 58. The configuration of the components of the davit assembly 54 will vary in size depending on the size of the reaction vessel 12 and the associated door 32. In one exemplary configuration, the upright davit 56 is made of an approximately six inch diameter tube with the door support arm 58 being made of approximately four inch diameter steel tube. The counterweight 64 in this configuration will vary to match the weight of the associated door 32, but in one embodiment, the counterweight 64 is made of steel and weighs approximately 250 pounds. The door support arm 58 attaches to the davit upright 56 by means of a T-connection 66. The T-connection 66 is rotatable about the davit upright 56 and includes a bearing (not shown) for rotation. The bearing can be a sleeve in which the davit assembly 54 rotates. The davit assembly 54 can be mounted with the base in any configuration. The davit can remain attached to the door during the entire process.

Figure 4:
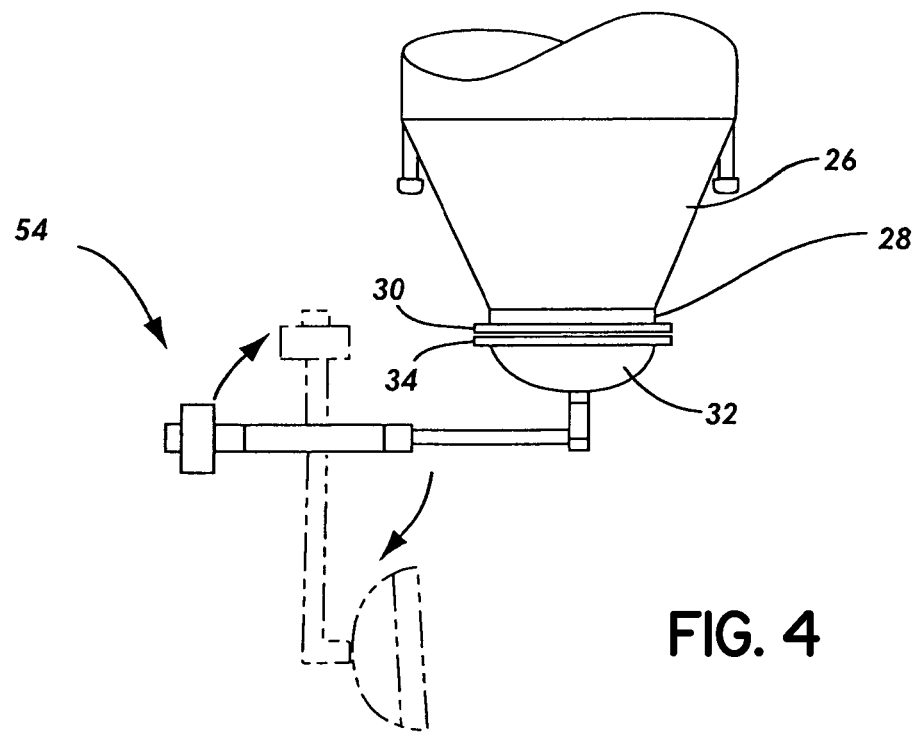
FIG. 4 is a top view of the davit and door assembly.

FIG. 4 shows a top view of the davit assembly 54. In the position shown in solid lines, the davit assembly 54 and the attached door 32 are in a closed position. The door 32 is positioned adjacent the first locking rim 30, which surrounds the access opening 52 on the cylindrical collar 28. Cylindrical collar 28 is attached to the frustoconical section 26.

Figure 21:
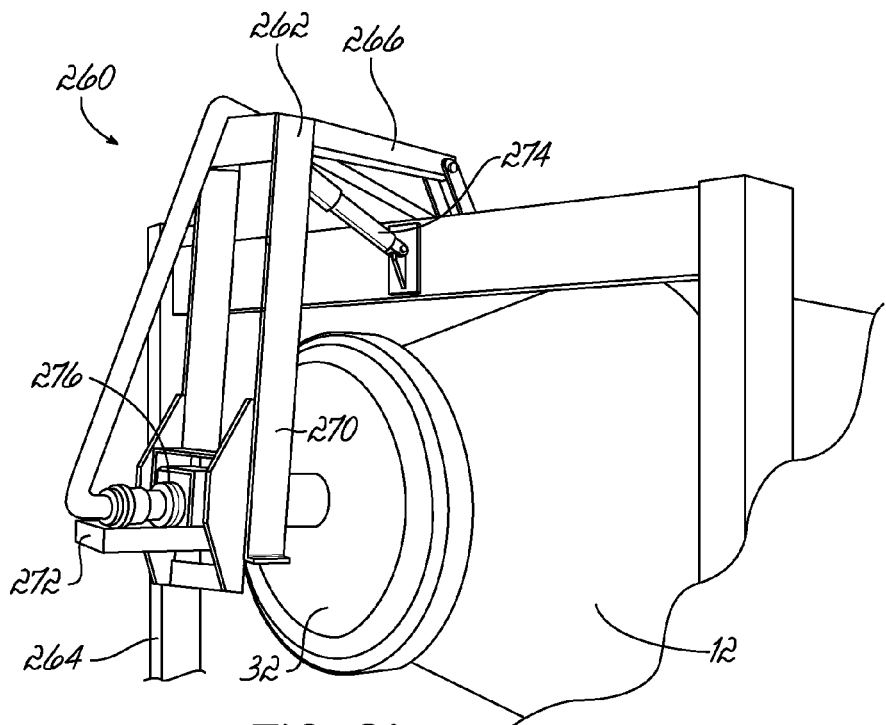
FIG. 21 is a perspective view of a reaction vessel with an elevating assembly.
Figure 22:
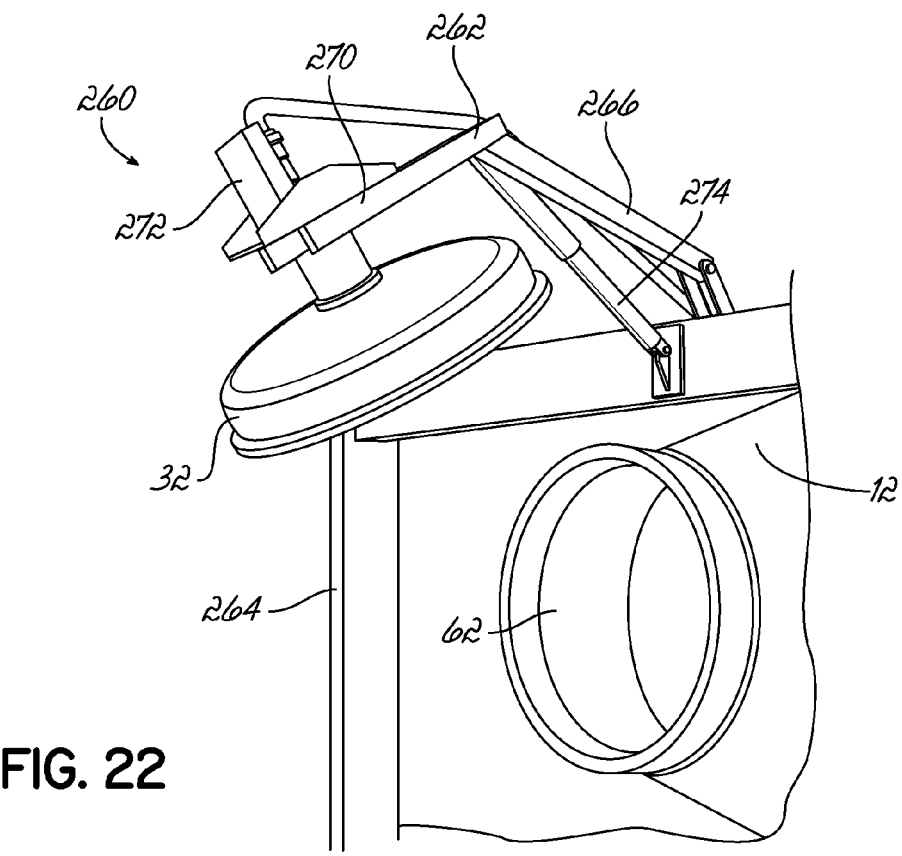
FIG. 22 is a perspective view of a reaction vessel with an elevating assembly.
Figure 23:
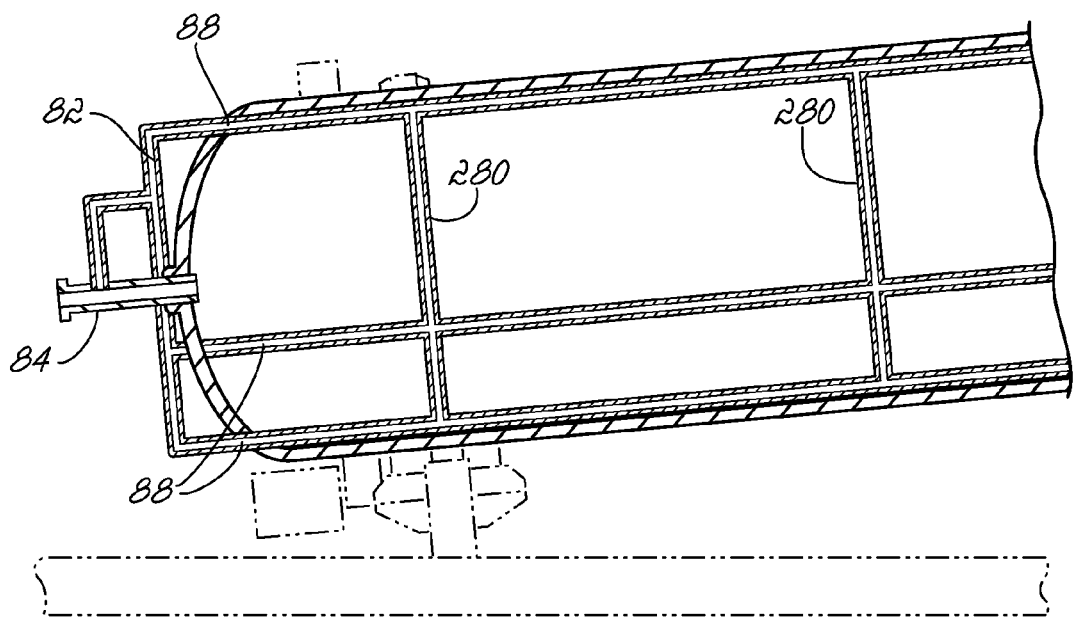
FIG. 23 is a cross-sectional view of a reaction vessel with both circumferential and longitudinal sparging lines.

An embodiment of the invention includes an elevating door assembly 260, as shown in FIGS. 21-22. The elevating assembly 260 includes a elevating support arm 262 and a supporting base 264. The first end 266 of the support arm 262 is pivotally coupled to the supporting base 264 located above the access opening 52 of the reaction vessel 12. The second end 270 of the support arm 262 is rotatably coupled to a nipple 278 on the door 32 by a boss 276. During operation, the boss 276 compactly supports the rotation of the door 32 and when combined with a concave door, results in a more compact coupling. The coupling between the boss 276 and the second end 270 may also include a mounting plate 272 and a support structure (not shown) that allows the boss 276 to move laterally and horizontally to accommodate eccentricities in the axis of rotation of the reaction vessel 12. For example, the mounting plate 272 may be coupled to the second end 270 of the elevating support arm 262 with the boss 276 coupled to mounting plate 272 by the support structure. The support structure may include pistons configured to allow horizontal and vertical movement or other such structures such as elastomeric members and/or pivoting members.

The elevating door assembly 260 is configured so that the elevating support arm 262 pivots about the coupling to the support base 264 allowing the access door 32 to move upward away from the access opening 52 or downward toward the access opening 52. This can be accomplished by known mechanisms including hydraulic actuators 274 coupled to the elevating support arms 262. The supporting base 264 extends above the reaction vessel 12 and may include a frame that rests on or is coupled to the floor or ground or that attached to a structure above the reaction vessel.

Figure 6:
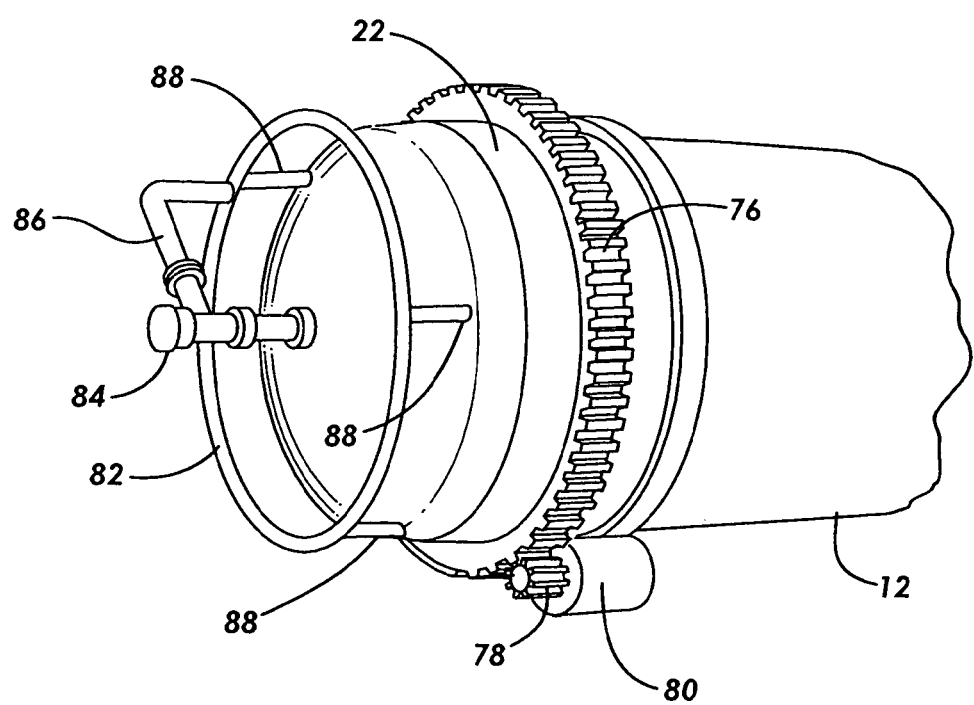
FIG. 6 is an end view of a cross section of the vessel.

FIG. 6 is a view of the second end 22 of the reaction vessel 12. In an embodiment of the invention, a gear ring 76 interacts with a drive gear 78 and a motor 80 to rotate the entire reaction vessel 12. Also seen on the second end 22 is a rounded ellipsoid head. The vessel 12 also includes a means for introducing steam into the interior of the vessel. As shown in the exemplary embodiment, steam may be injected into the vessel through a circular steam sparger manifold 82. Steam is injected into the sparger manifold 82 by means of a rotary joint 84 and a steam connector line 86. From the sparger manifold 82, a number of sparger lines 88 extend into the interior of the reaction vessel 12. In this configuration, these longitudinal sparger lines are straight and attached to the interior wall and run the length of the reaction vessel 12. These lines are also shown in FIG. 7. While they are shown in FIG. 7 as protruding through the opposite end of the reaction vessel 12 and being terminated there, the ends of the sparging lines 88 could also be linked to each other so that if an obstruction blocked one sparging line, the line could be pressurized beyond the obstruction from the other end. As shown is FIG. 23, the longitudinal sparging lines 88, can be coupled to one another within the vessel by one or more circumferential sparging lines 280 that run around the inner circumference of the reaction vessel. Thus, the steam sparging lines, both longitudinal 88 and circumferential 280, penetrate the auger vanes where the auger vanes are attached to the vessel wall and both include orifices for injecting steam. In one embodiment, the reaction vessel 12 includes at least three circumferential sparging lines 280. It will further be appreciated that the means for introducing steam into the interior of the vessel can further include other devices such as sparging lines, ports from the heated jacket to vessel's interior, a steam generator, or any other device for introducing steam into a vessel. An additional desirable feature is a steam outlet on the access door of the vessel 12, and valving which allows use of the rotary joint for evacuation of steam from the vessel 12.

FIG. 7 is an elevational view of biomass bearing material treatment vessel 10. Shown is the reaction vessel 12 with a first trunnion assembly 14 and a second trunnion assembly 16. The reaction vessel 10 is held at an angle from about 2 degrees to about 10 degrees, depending on the selections of the operator. The first end 24 of the reaction vessel includes a frustoconical section 26, a cylindrical collar 28, and a first locking rim 30. Auger vanes 36 are shown attached to the inner wall of the reaction vessel and form a spiral the length of the reaction vessel 12. The height of the auger vane decreases towards the first end 24. At the second end 22 of the reaction vessel, a circular steam sparger manifold 82 is seen. This connects to a steam connector line 86 and a rotary joint 84. A number of longitudinal sparger lines 88, which extend into the reaction vessel 12, extend from the steam sparger manifold 82. Orifices (not shown) in the longitudinal sparger lines 88 and the circumferential sparger lines 280 allow steam to exit the sparger lines into the reaction vessel 12.

FIG. 6 is a view of the second end 22 of the reaction vessel 12. In one embodiment, a gear ring 76 interacts with a drive gear 78 and a motor 80 to rotate the entire reaction vessel 12. Also seen on the second end 22 is a rounded ellipsoid head. Steam is injected into the vessel through a circular steam sparger manifold 82. Steam is injected into the sparger manifold 82 by means of a rotary joint 84 and a steam connector line 86. From the sparger manifold 82, a number of longitudinal sparger lines 88 extend into the interior of the reaction vessel 12. In this configuration, the longitudinal sparger lines are straight and attached to the interior wall of the reaction vessel 12. These lines are also shown in FIG. 7. While they are shown in FIG. 7 as protruding through the opposite end of the reaction vessel 12 and being terminated there, the ends of the sparging lines 88 could also be linked to each other so that if an obstruction blocked one sparging line, the line could be pressurized beyond the obstruction from the other end. A desirable feature is a steam outlet on the door 32 of the vessel 12, and valving which allows use of the rotary joint 276 for evacuation of steam from the vessel.

FIG. 7 is an elevational view of the biomass bearing material treatment vessel 10. Shown is the reaction vessel 12 with a first trunnion assembly 14 and a second trunnion assembly 16. The reaction vessel 10 is held at an angle from 2-10 degrees, depending on the selections of the operator. The first end 24 of the reaction vessel includes a frustoconical section 26, a cylindrical collar 28, and a first locking ring 30. Auger vanes 36 are shown attached to the inner wall of the reaction vessel and form a spiral the length of the reaction vessel 12. The height of the auger vane decreases towards the first end 24. At the second end 22 of the reaction vessel, a circular steam sparger manifold 82 is seen. This connects to a steam connector line 86 and a rotary joint 84. A number of sparger lines 88, which extend into the reaction vessel 12, extend from the steam sparger manifold 82. Orifices (not shown) in the sparger lines 88 allow steam to exit the sparger lines into the reaction vessel 12.

The first trunnion assembly 14 includes trunnions 20 and tracks 18, which circumvolve the reaction vessel 12. The reaction vessel 12 is turned by a motor 80, which drives a drive gear 78 that interacts with a gear ring 76 attached to the reaction vessel 12, causing the reaction vessel 12 to rotate on the trunnion assembly. It is to be understood that although two trunnion assemblies 14, 16 are shown, a pair of trunnions at each trunnion assembly supports the reaction vessel 12. Thus, each tract may be supported by two trunnions, and in this embodiment, the reaction vessel is supported by four trunnions.

FIG. 8 shows an end view of the first end 24 of the reaction vessel 12. Shown is the gear ring 76, which circumvolves the reaction vessel 12. The door 32 is shown in its position covering the access opening. The first section 42 of the clamp collar is shown, as well as the second section 44 of the clamp collar. The first clamp collar screw 48 and the second clamp collar screw 50 are shown. The clamp collar 40 is shown in an open position in solid lines and in a closed position in dashed lines. As shown, the clamp collar screws 48 and 50 extend from a motor housing 68 in which preferably two separate motors turn the clamp collar screws and cause the sections of the clamp collar to come together or move apart. Trunnion 20 is shown supporting the reaction vessel 12. Also shown is drive gear 78, which is driven by a motor 80.

Figure 24:
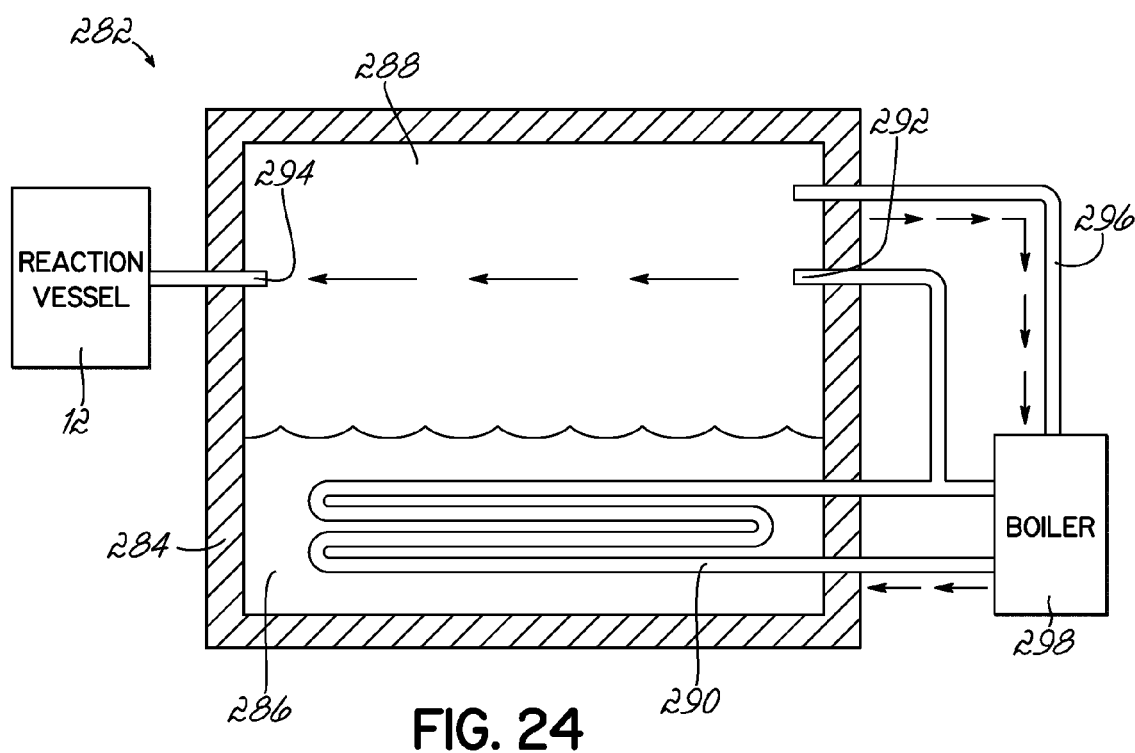
FIG. 24 is cross-sectional view of a steam charging chamber.

In operation, same embodiments of the invention utilize a process for quickly charging the vessel with steam in a shortened period of time compared to older methods, such as less than about 30 minutes. Various elements contribute to the vessel's capability to be quick charged including the longitudinal and circumferential sparging lines 88, 280, and the heated jacket 200, shown in FIGS. 13 and 23, respectively. Another element useful for quick charging the vessel 12 is a steam charging chamber 282 as shown in FIG. 24. The steam charging chamber 282 includes a sealed pressure chamber 284 configured to hold a volume of water 286 while leaving a headspace 288 above the volume of water 286, a heating coil 290 below the volume of water 286, a steam inlet 292 in the headspace 288, a steam outlet 294 from the headspace 288 to the reaction vessel 12, and a line 296 to return steam injected into the headspace 288 for another use or to recycle the steam back to boiler 298. The charging chamber 282 functions by first heating the water 286 with a heated medium, such as steam, circulating the heating coil 290. As the water 280 is heated, pressure builds in the headspace 288. Once a critical pressure is reached in the head space 286, steam is injected into the headspace 288 causing rapid expansion of the steam in the headspace 288 that is available for quick charging the reaction vessel 12. The steam from the head space 288 is channeled to the reaction vessel 12 where it may be used to heat the heated jacket 200 and/or quick charge the interior of the reaction vessel 12. In one embodiment, the operating pressure of the reaction vessel 12 is reached in less that about 30 minutes. In another embodiment, the operating pressure is reached in less than about 20 minutes. In another embodiment, the operating pressure is reached in less than 15 minutes.

Thus, embodiments of the invention are useful in a method of separating the cellulosic fraction from a waste stream that includes biomass. The methods includes adding the waste to a sealable reaction vessel, quick charging the vessel with steam to an operating pressure in a shortened period of time, such as in less than about 30 minutes, or less than about 20 minutes, or less than about 15 minutes. The vessel is rotated at the operating pressure to separate the cellulosic fraction from the other fractions of the waste. The vessel may optionally include a heated jacket and raised projections on auger vanes. The raised projections improve the operation of the vessel by increasing the mechanical agitation of the waste by the auger vanes. In one embodiment, cupped projections further improve on the agitation of the raised projections and the auger vanes by agitating the waste stream to quickly expose the waste to steam. Moreover the cupped projections being angled toward the door of the vessel serve to efficiently fluff the waste as it is being processed and to remove the product after processing.

Figure 11:
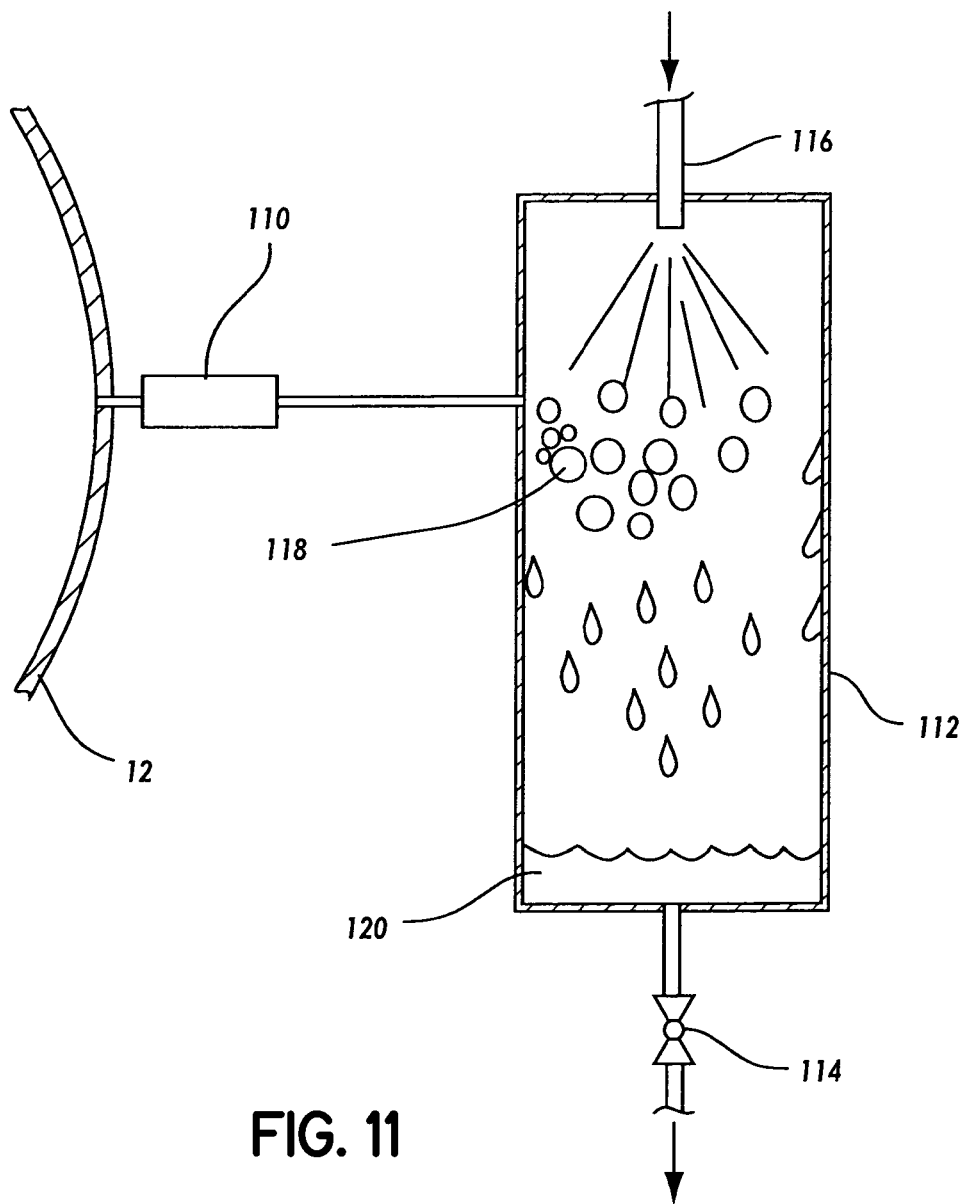
FIG. 11 is a view of the effluent system.

FIG. 11 shows a view of the effluent system 109 to capture vapors and process steam from the reaction vessel 12. The effluent system 109 in the reaction vessel 12 includes a steam eductor 110 and a barometric condenser 112. The barometric condenser 112 can take various forms and would of course be sized according to the particular design of the reaction vessel 12. One version of the barometric condenser 112 can include a condensation tank, which is approximately three feet in diameter and six feet tall, and is oriented vertically. A connection between the tank and the reaction vessel is made so that steam from the reaction vessel can be allowed to enter the tank at a point about two thirds from the bottom of the tank. As the steam 118 from the reaction vessel enters the tank, it is condensed. This can be done in several ways. A very effective method is to spray water 116 from the top of the tank onto the steam 118. This not only condenses the gaseous steam into a condensate liquid 120, but in doing so, also creates a vacuum, which pulls more steam from the reaction vessel. One effect of this is that the volume of effluents from the barometric condenser 112 is increased, and the concentration of contaminants from the steam is decreased. There is also a drain valve 114 for removing the condensate 120.

Other methods of condensing water from the steam are also possible, such as having the steam hit tubes filled with a cool liquid, which would require a refrigeration unit to keep the liquid in the tubes cool. Cold air can also be injected into the condensation tank, which would result in less volume of eventual effluent, but with a higher concentration.

The steam eductor is the device that extracts the atmosphere from the reaction vessel and directs it into the barometric condenser. The steam eductor can take a number of forms including an air pump, venturi tube or any other commonly used device that moves air. The steam eductor would be utilized to remove as much steam from the reaction vessel as possible before it is opened. The removal of this atmosphere can continue until there is a negative pressure in the reaction vessel.

Even with a thorough evacuation and flushing of the atmosphere from the reaction vessel, when the door to the reaction vessel is opened and the feedstock material is moved by the augers to the opening, the act of stirring, tumbling, and moving the feedstock material by the reaction vessels and the augers, the feedstock material will release significant quantities of steam. To capture this steam, a hood, which is placed over the door to the reaction vessel so that effluents from the feedstock material can be enclosed in the hood and drawn off to the barometric condenser, is useful. After processing, the biomass bearing material in the reaction vessel is referred to as feedstock, to reflect the change in the physical and chemical makeup of the material. Typically, the feedstock and non-cellulosic material from the reaction vessel are directed to a trommel screen for sorting of the material. While the recently heated feedstock is on the trommel screen and being moved, steam will continue to be released. A hood over the trommel screen is effective at this point to contain steam and gaseous effluents, and to allow them to be channeled to the barometric condenser.

While there is shown and described the exemplary embodiments of the invention, it is to be distinctly understood that this invention is not limited thereto but may be variously embodied to practice within the scope of the following claims. From the foregoing description, it will be apparent that various changes may be made without departing from the spirit and scope of the invention as defined by the following claims.

What is claimed is:

1. A biomass bearing material treatment pressure and steam containing vessel, comprising:
    a generally cylindrical rotatable reaction vessel having first and second ends on a rotational axis, said reaction vessel configured for rotation;
    at least one access opening to an interior of said reaction vessel, and through which biomass bearing material may pass;
    a concave door for closing said access opening, wherein said concave door has an outer surface defining a cavity;
    a door sealing system operatively associated with said door for sealing said door to said vessel at said access opening and for maintaining a pressure differential between the interior of said vessel and an exterior thereof wherein at least a portion of said door sealing system is disposed in the cavity of the concave door; and
    at least one flight of auger vanes on an interior wall of said reaction vessel and extending into the interior of said vessel in a plane, for moving biomass bearing material within said vessel from said first end to said second end of said reaction vessel, and from said second end to said first end of said reaction vessel, said auger vanes having a base edge attached to an interior vessel wall;
    wherein the door sealing system comprises a first locking rim surrounding said access opening on the reactor vessel; a second locking rim on said door for placement adjacent the first locking rim, a clamp collar and at least one clamp screw coupled to the outer surface of the door by a bearing disposed in the cavity;
    wherein said clamp collar comprises a first section coupled to a first threaded boss and a second section coupled to second threaded boss, and the at least one clamp screw engaging the bearing and at least one of the first and second threaded bosses for drawing the first and second sections together for sealing said door over the access opening.

2. The vessel of claim 1 in which the first and second sections forms the outermost perimeter of the door sealing system.

3. The vessel of claim 1 in which said cylindrical reaction vessel is configured for adjustability an angle of the vessel from horizontal.

4. The vessel of claim 1 further comprising a means for introducing steam into the interior of the reaction vessel.

5. The vessel of claim 4 wherein the means for introducing steam includes a plurality of sparging lines operably connected to an interior of said vessel for injecting steam into said vessel.

6. The vessel of claim 5 further comprising a steam charging chamber operatively connected to the plurality of steam sparging lines.

7. The vessel of claim 1 further comprising a third threaded boss couple to the first section and a fourth threaded boss coupled to the second section and wherein the at least one clamp screw includes a first clamp screw and a second clamp screw, the first clamp screw engaging at least one of the first threaded boss or the second threaded boss and the second clamp screw engaging at least one of the third threaded boss or the fourth threaded boss.

8. The vessel of claim 1 wherein the first section further includes a first cross member and the second section further includes a second cross member, wherein the first cross member couples the first threaded boss to the first section and the second cross member couples the second threaded boss to the second section.

9. The vessel of claim 1 further comprising a motor coupled to the door configured to turn the at least one clamp screw.

10. The vessel of claim 1 further comprising at least one bearing coupled to the door and anchoring the at least one clamp screw.

11. A biomass bearing material treatment pressure and steam containing vessel, comprising:
    a generally cylindrical rotatable reaction vessel having first and second ends on a rotational axis, said reaction vessel configured for rotation;
    a heated jacket wherein said heated jacket includes an outer covering and a structure for circulating a heated media around the outer surface of the reaction vessel, said structure having at least one channel in fluid communication with a source of heated media via a rotary joint, wherein the channel wraps around the circumference of the vessel from at least near the first end of the vessel to at least near the second end of the vessel;
    at least one access opening to an interior of said reaction vessel, and through which biomass bearing material may pass;
    a door for closing said access opening;
    a door sealing system operatively associated with said door for sealing said door to said vessel at said access opening and for maintaining a pressure differential between the interior of said vessel and an exterior thereof;
    at least one flight of auger vanes on an interior wall of said reaction vessel and extending into the interior of said vessel in a plane, for moving biomass bearing material within said vessel from said first end to said second end of said reaction vessel, and from said second end to said first end of said reaction vessel, said auger vanes having a base edge attached to an interior vessel wall.

12. The vessel of claim 11 wherein the structure for circulating heated media allows the heated media to contact the outer surface of the vessel.

13. The vessel of claim 11 wherein the outer covering includes an inner surface and the at least one channel is formed by a vane extending between the inner surface of the outer covering and the outer surface of the vessel.

14. The vessel of claim 11 wherein the channel wraps around the circumference of the vessel from a first end of the vessel to a second end of the vessel and then back to the first end of the vessel.

15. The vessel of claim 11 wherein the at least one channel is formed by tubing located between the outer covering and the outer surface of the vessel.

* * * * *